United States Patent
Volgyesi

(10) Patent No.: US 10,828,459 B2
(45) Date of Patent: Nov. 10, 2020

(54) BREATH POWERED POSITIVE AIRWAY PRESSURE DEVICE

(71) Applicant: George Volgyesi, Willowdale (CA)

(72) Inventor: George Volgyesi, Willowdale (CA)

(*) Notice: Subject to any disclaimer, the term of this patent is extended or adjusted under 35 U.S.C. 154(b) by 210 days.

(21) Appl. No.: 16/119,684

(22) Filed: Aug. 31, 2018

(65) Prior Publication Data

US 2018/0369535 A1     Dec. 27, 2018

Related U.S. Application Data

(63) Continuation-in-part of application No. 15/145,940, filed on May 4, 2016, now Pat. No. 10,576,241.

(51) Int. Cl.
| | | |
|---|---|---|
| *A61M 16/20* | (2006.01) | |
| *A61M 16/08* | (2006.01) | |
| *A61M 16/06* | (2006.01) | |

(52) U.S. Cl.
CPC ...... *A61M 16/208* (2013.01); *A61M 16/0866* (2014.02); *A61M 16/0875* (2013.01); *A61M 16/201* (2014.02); *A61M 16/06* (2013.01); *A61M 2205/0272* (2013.01)

(58) Field of Classification Search
CPC ............ A61M 16/006; A61M 16/0075; A61M 16/0078; A61M 16/009; A61M 16/0866; A61M 16/0875; A61M 16/201; A61M 16/205; A61M 16/208; A61M 16/209
See application file for complete search history.

(56) References Cited

U.S. PATENT DOCUMENTS

| | | | |
|---|---|---|---|
| 3,216,413 A * | 11/1965 | Arecheta Mota | ............................ A61M 16/0009 128/205.13 |
| 7,506,649 B2 | 3/2009 | Doshi et al. | |
| 2002/0104538 A1* | 8/2002 | Emtell | .............. A61M 16/0078 128/205.14 |
| 2010/0163046 A1* | 7/2010 | Fisher | ................. A61M 16/107 128/204.18 |
| 2013/0118498 A1* | 5/2013 | Robitaille | ......... A61M 16/0866 128/205.16 |

(Continued)

FOREIGN PATENT DOCUMENTS

EP     2 106 819 A1     10/2009

OTHER PUBLICATIONS

Kakkar RK, Berry RB. "Positive airway pressure treatment for obstructive sleep apnea." Chest. Sep. 2007; 132 (3) 1057-72 (Abstract).

(Continued)

*Primary Examiner* — Valerie L Woodward

(57) ABSTRACT

A breath powered positive airway pressure device having an expiratory chamber for receiving expired air from a user. The chamber has at least one resiliently flexible surface that is configured to expand to accommodate the expired air, so that the pressure within the chamber gradually increases during expiration. The device may also include an inspiratory chamber for holding air to be inspired, wherein the at least one resiliently flexible surface forms a flexible partition separating the expiratory chamber from the inspiratory chamber. The flexible partition is configured to expand into the inspiratory chamber during expiration, so that the air that is held within the inspiratory chamber also becomes pressurized during expiration.

24 Claims, 28 Drawing Sheets

(56) References Cited

U.S. PATENT DOCUMENTS

2014/0261425 A1    9/2014    Connor

OTHER PUBLICATIONS

Kapll Chaudhary and Munisha Agarwal, "An innovative nasal continuous positive airway pressure assembly", Indian J Crit Care Med. Mar.-Apr. 2013; 17(2): 104-106 (Abstract).
Rossi VA et al. "The effects of Provent on moderate to severe obstructive sleep apnea during continuous positive airway pressure therapy withdrwal: a randomised controlled trial" Thorax. Sep. 2013; 68 (9): 854-9 (Abstract).
Friedman M et al., "Provent therapy for obstructive sleep apnea: Impact of nasal obstruction" Laryngoscope. Apr. 17, 2015. (Abstract).
Leon Rosenthal, M.D. et al. "A Multicenter, Prospective Study of a Novel Nasal EPAP Device in the treatment of obstructive sleep Apnea: Efficacy and 30-Day Adherence", JCSM, vol. 5, No. 6, 2009.
Peter Gay, M.D. et al., "Evaluation of Positive Airway Pressure Treatment for Sleep Related Breathing Disorders in Adults", Sleep, vol. 29, No. 3, 2006.
Molina Healthcare "Expiratory Positive Airway Pressure (EPAP) for Obstructive Sleep Apnea".
Rajiv Doshi and Philip Westbrook, "Nasal Expiratory Positive Airway Pressure (EPAP) for Treatment of Obstructive Sleep Apnea" Respiratory Therapy vol. 6, No. 4 Aug.-Sep. 2011.
Glenn Adams, Nasal Expiratory Positive Airway Pressure (EPAP) Device to Treat Obstructive Sleep Apnea in Medicare Age Patients (Age >65).
Provent Product Information Sheet.
Victor Hoffstein "Review of oral appliances for treatment of sleep-disordered breathing" Sleep Breath (2007) 11:1-22.
Blaylock, "Immune Activation: Vaccines and the Developing Brain", The Vaccine Choice Journal, 4.1 (2017): 1-28.
White, "Auto-PEEP to Treat Obstructive Sleep Apnea", Journal of Clinical Sleep Medicine, 5.6 (2009): 538-539.
Berry et al., "A Novel Nasal Expiratory Positive Airway Pressure (EPAP) Device for the Treatment of Obstructive Sleep Apnea: A Randomized Controlled Trial", Sleep, 34.4 (2011).
Ginosar et al., "High Altitude, Continuous Positive Airway Pressure, and Obstructive Sleep Apnea Subjective Observations and Objective Data", High Altitude Medicine & Biology, 14.2 (2013): 186-189.
T.S. Hakim et al., "Obstructive Sleep Apnea Treatment with EPAP Nasal Devices: Physiological Principles and Limitations", Journal of Sleep and Sleep Disorder Research, 1.1 (2017): 33-41.
Lipman et al., "Study Looking at End Expiratory Pressure for Altitude Illness Decrease (SLEEP-AID)", High Altitude Medicine & Biology, 16.2 (2015): 1-8.
Banner et al., "Effects of Expiratory Flow Resistance on Inspiratory Work of Breathing", Chest, 93.4 (1988): 795-799.
Johnson et al., "Non-Invasive Positive Pressure Ventilation during Sleep at 3800m: relationship to Acute Mountain Sickness and sleeping oxyhemoglobin saturation", Respirology, 15.2 (2010): 277-282.
Johnson et al., "Continuous Positive Airway Pressure Treatment for Acute Mountain Sickness at 4240 m in the Nepal Himalaya", High Altitude Medicine & Biology, 14.3 (2013): 230-233.

\* cited by examiner

BREATH POWERED POSITIVE AIRWAY PRESSURE DEVICE

RELATION APPLICATIONS

This application is a continuation-in-part application of prior U.S. application Ser. No. 15/145,940 filed May 4, 2016, the entire contents of which is incorporated herein by reference.

FIELD OF THE INVENTION

This invention relates to positive airway pressure devices for treating obstructive sleep apnea and other breathing conditions. More particularly, the invention provides a breath powered device that can provide positive airway pressure without requiring an external power source.

BACKGROUND OF THE INVENTION

Continuous positive airway pressure (CPAP) machines are commonly used in the treatment of obstructive sleep apnea. These machines deliver a continuous stream of air to a patient's airway, producing a positive pressure that keeps the patient's airway open and allows for unobstructed breathing. Although CPAP machines provide an effective treatment for sleep apnea, they generally require electricity to operate. As such, the long term use of these machines may be costly for patients. They may also be inoperable in situations where electricity is unavailable, such as during power outages and in remote locations.

Nasal expiratory positive airway pressure (EPAP) devices, such as Provent™ and Theravent™, provide positive airway pressure during expiration, without requiring electricity. These small, disposable devices are temporarily affixed to a user's nostrils, and incorporate vents that are designed to open while the user inhales, and to partially close while the user exhales. The increased resistance during expiration produces positive airway pressure, which may be effective in treating conditions such as obstructive sleep apnea and snoring.

These EPAP devices do not, however, provide positive airway pressure during inspiration. Nor do they allow for control of respiratory parameters such as pressure, flow and tidal volume. Furthermore, some nasal EPAP devices may produce significant airway resistance during expiration and inspiration, which increases the work of breathing and may lead to Upper Airway Resistance Syndrome (UARS). Additionally, the devices may potentially become clogged with nasal secretions, rendering them useless or even dangerous in some circumstances.

SUMMARY OF THE INVENTION

To at least partially overcome some of the disadvantages of previously known devices, the invention provides a breath powered positive airway pressure device. The device incorporates an expiratory chamber for receiving a user's expired air. The expiratory chamber has at least one resiliently flexible surface that is configured to expand to accommodate the expired air. As the expired air collects in the expiratory chamber, the flexible surface expands outwardly and the pressure within the chamber gradually increases. This pressurized air is used to provide positive airway pressure to the user.

The resiliently flexible surface permits the volume of the chamber to increase as the expired air is collected therein, so that the pressure within the chamber rises gradually. As the commencement of expiration is not restricted by high resistance, the device may allow for more comfortable and natural breathing. In preferred embodiments, the device is fully adjustable so that pressure, flow and/or volume parameters may be selected to best suit each user's individual needs. Furthermore, as the device uses the user's own breath to produce the positive airway pressure, it can be operated without requiring an external power source.

The device includes an airway connector configured to receive expired air from the user. The airway connector can optionally be in the form of a nasal pillow, a nose mask, a full-face mask, or in any other suitable form for interfacing, directly or indirectly, with the user's airway. In some embodiments of the invention, a one-way expiration valve is interposed between the airway connector and the expiratory chamber, so as to permit the expired air to pass from the airway connector to the expiratory chamber, while preventing the expired air from passing back from the expiratory chamber into the airway connector. Optionally, the one-way expiration valve may be included as part of a non-rebreathing apparatus or valve assembly.

Some embodiments of the device also include an inspiratory chamber, for delivering air to be inspired by the user. The inspiratory chamber is preferably positioned adjacent to the expiratory chamber, with the resiliently flexible surface forming a partition therebetween. This arrangement permits both the expiratory chamber and the inspiratory chamber to become pressurized, so as to provide positive airway pressure during both expiration and inspiration. In particular, when the expiratory chamber becomes pressurized during expiration, the resiliently flexible surface expands into the inspiratory chamber, compressing and pressurizing the air to be inspired that is held therein.

The device may also incorporate any desired arrangement of valves and openings for allowing the expired air to exit the device and the air to be inspired to enter the device, and for controlling or moderating flow rates and pressures within the expiratory and inspiratory chambers. For example, the device may incorporate one or more pressure control valves that release expired air from the expiratory chamber when the pressure therein exceeds a threshold pressure. These valves can be used to set maximum and minimum pressures within the chambers, so that the positive airway pressure that is provided falls within an optimized, preselected range. Preferably, the pressure control valves are adjustable so that the pressure limits can be set based on each user's individual needs.

In some embodiments of the invention, a flexible conduit connects the expiratory chamber to an air outlet, for releasing expired air from the chamber. The dimensions of the flexible conduit are selected so that the flow rate of the expired air exiting the expiratory chamber through the conduit is lower than the flow rate of expired air entering the expiratory chamber during expiration, so that the expiratory chamber becomes pressurized during expiration.

The inspiratory chamber may also have a resiliently flexible wall, with an occluder interposed between the flexible wall and the flexible conduit. During expiration, the resiliently flexible surface of the expiratory chamber expands into the inspiratory chamber, pressurizing the air to be inspired that is held therein. The increased pressure within the inspiratory chamber furthermore causes the flexible wall to expand outwards, pushing the occluder into engagement with the flexible conduit. This closes the flexible conduit, preventing the expired air from being released from the air outlet, and thus ensuring that the expiratory chamber and the inspiratory chamber remain pressurized at least at the beginning of inspiration.

During inspiration, the user draws the pressurized air from the inspiratory chamber, which reduces the pressure therein. This allows the flexible wall to retract away from the flexible conduit, disengaging the occluder from the conduit. With the conduit open, the expired air can be released from the expiratory chamber, and the pressure within the chambers can return to a baseline level before expiration begins again.

Accordingly, in at least one aspect the present invention resides in a breath powered positive airway pressure device comprising: an airway connector configured to receive expired air from a user; an expiratory chamber in fluid communication with the airway connector, for receiving the expired air therefrom, the expiratory chamber having at least one resiliently flexible surface that is configured to expand to accommodate the expired air; a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and an air outlet in fluid communication with the expiratory chamber, for releasing the expired air therefrom; wherein the air outlet is configured to release the expired air from the expiratory chamber more slowly than the expired air enters the expiratory chamber during expiration, so that the expired air within the expiratory chamber becomes pressurized during expiration.

The positive airway pressure device may further include a non-rebreathing valve assembly interposed between the airway connector and the expiratory chamber, the non-rebreathing valve assembly comprising: an expiration port in fluid communication with the expiratory chamber; the one-way expiration valve, which is interposed between the airway connector and the expiration port; an inspiration port for receiving air to be inspired by the user; and a one-way inspiration valve interposed between the airway connector and the inspiration port, the one-way inspiration valve permitting the air to be inspired to pass from the inspiration port to the airway connector, and preventing the expired air from passing from the airway connector to the inspiration port.

The positive airway pressure device may further include a pressure control valve in fluid communication with the expiratory chamber; wherein the pressure control valve is configured to open, to release some of the expired air from the expiratory chamber, when a pressure within the expiratory chamber exceeds a threshold pressure, and to close when the pressure within the expiratory chamber is at or below the threshold pressure.

Preferably, the pressure control valve is adjustable to select the threshold pressure. In some embodiments the pressure control valve is configured to maintain the pressure within the expiratory chamber at or below the threshold pressure. In some embodiments the pressure control valve is configured to maintain the pressure within the expiratory chamber at or above the threshold pressure.

The positive airway pressure device may further include an inspiratory chamber for holding the air to be inspired, the inspiratory chamber in fluid communication with the inspiration port; and a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve; wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized.

In some embodiments, the inspiratory chamber has a resiliently flexible wall and the positive airway pressure device further comprises: a flexible conduit interposed between, and in fluid communication with, the expiratory chamber and the air outlet; and an occluder interposed between the resiliently flexible wall and the flexible conduit; wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; and wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet.

Preferably, the expiratory chamber and the inspiratory chamber are configured so that, during a normal breathing cycle, the expiratory chamber and the inspiratory chamber are pressurized at the end of expiration and at the beginning of inspiration, and are depressurized to a baseline pressure at the end of inspiration.

In some embodiments, the positive airway pressure device is exclusively breath powered.

Optionally, the air outlet is adjustable to select a rate at which the expired air is released from the expiratory chamber; and the at least one resiliently flexible surface is adjustable to select a rate at which the pressure within the expiratory chamber increases during expiration.

In another aspect, the present invention resides in a method of providing breath powered positive airway pressure, comprising: expiring into a breath powered positive airway pressure device comprising: an airway connector configured to receive expired air from a user; an expiratory chamber in fluid communication with the airway connector, for receiving the expired air therefrom, the expiratory chamber having at least one resiliently flexible surface that is configured to expand to accommodate the expired air; a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and an air outlet in fluid communication with the expiratory chamber, for releasing the expired air therefrom; wherein the air outlet is configured to release the expired air from the expiratory chamber more slowly than the expired air enters the expiratory chamber during expiration, so that the expired air within the expiratory chamber becomes pressurized during expiration; and wherein the expiring comprises expiring into the airway connector so that the expired air within the expiratory chamber becomes pressurized and the at least one resiliently flexible surface expands.

In some embodiments, the positive airway pressure device further comprises a non-rebreathing valve assembly interposed between the airway connector and the expiratory chamber, the non-rebreathing valve assembly comprising:

an expiration port in fluid communication with the expiratory chamber; the one-way expiration valve, which is interposed between the airway connector and the expiration port; an inspiration port for receiving air to be inspired by the user; and a one-way inspiration valve interposed between the airway connector and the inspiration port, the one-way inspiration valve permitting the air to be inspired to pass from the inspiration port to the airway connector, and preventing the expired air from passing from the airway connector to the inspiration port; and the method further comprises inspiring through the airway connector.

In some embodiments, the positive airway pressure device further comprises a pressure control valve in fluid communication with the expiratory chamber; wherein the pressure control valve is configured to open, to release some of the expired air from the expiratory chamber, when a pressure within the expiratory chamber exceeds a threshold pressure, and to close when the pressure within the expiratory chamber is at or below the threshold pressure; wherein the pressure control valve is adjustable to select the threshold pressure; and the method further comprises adjusting the pressure control valve to select the threshold pressure.

In some embodiments, the positive airway pressure device further comprises: an inspiratory chamber for holding the air to be inspired, the inspiratory chamber in fluid communication with the inspiration port; and a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve; wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized; and the expiring comprises expiring into the airway connector so that the expired air within the expiratory chamber becomes pressurized and the flexible partition expands into the inspiratory chamber, thereby pressurizing the air to be inspired that is held within the inspiratory chamber; and the inspiring comprises inspiring, through the airway connector, the pressurized air that is held within the inspiratory chamber.

In some embodiments, the inspiratory chamber has a resiliently flexible wall and the positive airway pressure device further comprises: a flexible conduit interposed between, and in fluid communication with, the expiratory chamber and the air outlet; and an occluder interposed between the resiliently flexible wall and the flexible conduit; wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet; and the expiring comprises expiring into the airway connector so that the expired air within the expiratory chamber becomes pressurized and the flexible partition expands into the inspiratory chamber, thereby pressurizing the air to be inspired that is held within the inspiratory chamber and causing the resiliently flexible wall to push the occluder into engagement with the flexible conduit, closing the flexible conduit and preventing the expired air from being released from the air outlet; and the inspiring comprises inspiring, through the airway connector, the pressurized air that is held within the inspiratory chamber so that the resiliently flexible wall retracts away from the flexible conduit, so that the occluder disengages from the flexible conduit, allowing the flexible conduit to open and permitting the expired air to be released from the air outlet.

In some embodiments, the inspiring further comprises allowing a sufficient volume of the expired air to be released from the air outlet so that the expiratory chamber and the inspiratory chamber are depressurized to a baseline pressure at the end of the inspiration.

In some embodiments, the expiring comprises expiring into the airway connector, while sleeping, to treat obstructive sleep apnea; and the inspiring comprises inspiring through the airway connector, while sleeping, to treat obstructive sleep apnea.

In some embodiments, the air outlet is adjustable to select a rate at which the expired air is released from the expiratory chamber; and the at least one resiliently flexible surface is adjustable to select a rate at which the pressure within the expiratory chamber increases during expiration; and the method further comprises: adjusting the air outlet to select the rate at which the expired air is released from the expiratory chamber; and adjusting the at least one resiliently flexible surface to select the rate at which the pressure within the expiratory chamber increases during expiration.

The inventor has appreciated that, in at least some preferred embodiments of the invention, the device can be operated without external power; can provide adjustable positive airway pressure at least during the beginning of inspiration and the end of expiration; does not produce excessive resistance or otherwise impede peak expiratory flow at the commencement of expiration; provides low flow resistance during both inspiration and expiration; is reusable without limit; has no components requiring disposal or refill; and is safe and effective.

In yet another aspect, the present invention provides a breath powered positive airway pressure device comprising an airway connector assembly for communicating air to and from a user, and a breath chamber assembly in fluid communication with the airway connector assembly, the breath chamber assembly being for increasing airway pressure during expiration and inspiration, wherein the breath chamber assembly comprises an expiratory chamber for receiving expired air from the user, an inspiratory chamber for holding inhalation air to be inspired by the user, and a resiliently flexible partition separating the expiratory and inspiratory chambers, and the airway connector assembly comprises an airway connector for directing the expired air from and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector, wherein the breath chamber assembly further comprises: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough;

and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet, wherein during said expiration, the flexible partition expands into and pressurizes the inspiratory chamber, thereby actuating the pneumatic valve to the closed position, and pressurizing the expiratory chamber, and wherein during said inspiration, the inspiratory chamber is depressurized, whereby the pneumatic valve moves to the open position to permit the expired air to be released through the air outlet, and depressurize the expiratory chamber.

In yet another aspect, the present invention provides a breath chamber assembly for increasing airway pressure during expiration and inspiration, the breath chamber assembly comprising an expiratory chamber for receiving expired air from the user, an inspiratory chamber for holding inhalation air to be inspired by the user, and a resiliently flexible partition separating the expiratory and inspiratory chambers, the breath chamber assembly further comprising: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough; and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet, wherein during said expiration, the flexible partition expands into and pressurizes the inspiratory chamber, thereby actuating the pneumatic valve to the closed position, and pressurizing the expiratory chamber, and wherein during said inspiration, the inspiratory chamber is depressurized, whereby the pneumatic valve moves to the open position to permit the expired air to be released through the air outlet, and depressurize the expiratory chamber.

In one embodiment, the breath chamber assembly is for use with an airway connector assembly comprising an airway connector for directing the expired air from and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector. It is to be appreciated that the breath chamber assembly is not strictly required for use with the airway connector, the airway connector assembly or the combination of the airway connector and the non-breathing valve assembly, provided that the breath chamber assembly is provided with a one-way flow of the expired air from the user to the expiratory chamber (i.e., the expired air is prevented from passing from the expiratory chamber to the user), and a one-way flow of the inhalation air form the inspiratory chamber to the user (i.e., the expired air is prevented from passing from the user to the inspiratory chamber).

Preferably, the one-way expiration valve prevents the expired air from passing from the expiratory chamber to the airway connector, and the one-way inspiration valve prevents the expired air from passing from the airway connector to the inspiratory chamber. In one embodiment, the airway connector assembly further comprises the non-breathing valve assembly, and a pair of corrugated hoses for fluid communication between the expiration port and the expiratory chamber, and between the inspiration port and the inspiratory chamber.

In one embodiment, at least one of the air outlet and the pneumatic valve are configured to release the expired air from the expiratory chamber more slowly than the expired air enters the expiratory chamber at the beginning of said expiration, and wherein the pneumatic valve is configured to be in the closed position at least at the end of the expiration and the beginning of the inspiration. By way of a non-limiting embodiment, the air outlet is distanced from the pneumatic valve to provide flow resistance to the expired air released through the air outlet. In another embodiment, the air outlet is configured to provide flow resistance or turbulent air flow therethrough, by for example including an increased length and/or irregular interior contact surface with the expired air.

In one embodiment, the inspiratory chamber comprises a resiliently flexible wall configured to expand outwardly during said expiration. Preferably, the flexible wall is disposed in an opposed orientation to the flexible partition. In one embodiment, the flexible wall or partition is formed with one or more elastomers selected from the group consisting of polyisoprene, polybutadiene, chloroprene, butyl rubber, halogenated butyl rubber, styrene-butadiene rubber, nitrile rubber, hydrogenated nitrile rubber, ethylene propylene rubber, epichlorohydrin rubber, polyacrylic rubber, silicone rubber, fluorosilicone Rubber, fluoroelastomer, perfluoroelastomers, polyether block amides, chlorosulfonated polyethylene, ethylene-vinyl acetate, thermoplastic elastomers, polysulfide rubber and elastolefin. It is to be appreciated that the flexible wall and partition may be prepared with any other flexible material, provided that the wall/partition are operable to expand under air pressure provided by the user's breathing and contract when that pressure is removed. In one embodiment, one or both of the flexible partition and wall are substantially planar when not expanded, and have a shape selected from the group consisting of circle, triangle, square, pentagon, hexagon, heptagon and octagon.

In one embodiment, the inspiratory chamber comprises first and second inspiratory cavities respectively in fluid communication with the one-way air inlet valve and the airway connector assembly, the flexible wall enclosing the second inspiratory cavity, and the inspiratory chamber further comprising a one-way inspiratory chamber valve permitting the inhalation air to pass from the first inspiratory cavity to the second inspiratory cavity, wherein during said expiration, the flexible partition expands into the first inspiratory cavity, thereby moving the inhalation air in the first inspiratory cavity towards the second inspiratory cavity, and expanding the flexible wall outwardly.

In one embodiment, the inspiratory chamber further comprises an internal chamber wall dividing the first and second inspiratory cavities, the one-way inspiratory chamber valve being disposed in the internal chamber wall, and the internal chamber wall being shaped to prevent inward contraction of the flexible wall into the inspiratory chamber, and contact between the flexible wall and the flexible partition. In one embodiment, the flexible partition is has a substantially circular shape, and the internal chamber wall and the first inspiratory cavity have a dome shape selected to receive or accommodate the flexible partition therein during said expiration, and the internal chamber wall is further selected to abut against the flexible wall during the inspiration.

In one embodiment, the breath chamber assembly further comprises an air conduit interposed between the inspiratory chamber and the pneumatic valve in fluid communication therewith, and the pneumatic valve comprises a poppet valve comprising a disk plug and a pneumatic valve actuator coupled to the plug, the actuator being in fluid communication with the air conduit, wherein the actuator is configured to actuate the plug to the closed position during said expiration, and to move the plug to the open position during said inspiration. In one embodiment, the air conduit comprises an air tubing. Preferably, the air conduit is interposed between the first inspiratory cavity and the pneumatic value. It has been envisioned that with preferred actuation of the pneumatic value with the air pressure in the first inspiratory cavity (in fluid communication with the one-way air inlet valve), during the inspiration the pneumatic valve may remain in the closed position longer to provide a longer period of pressurization in the inspiratory chamber overall.

In one embodiment, the disk plug comprises a contact surface positioned for the fluid sealing contact with the air outlet in the closed position, the contact surface having a surface area that is at least 1.2 times greater than the air outlet, and the valve actuator comprises an expandable membrane coupled to the plug, wherein during said expiration, the expandable membrane expands to move the plug in said fluid sealing contact with the air outlet in the closed position. In one embodiment, the surface area is at least 1.5, 2.0, 2.5 or 3.0 times great than the air outlet. It has been appreciated that a force required to actuate the poppet valve against an air flow or pressure at the air outlet is affected by the relative sizes of the disk plug and the air outlet. Specifically, it has been appreciated that the greater the disk plug size relative to the air outlet, the less force or pressure required to close the air outlet. It has thus been envisioned that by selecting the contact surface of the disk plug to be larger than the air outlet, it may require less pressure in the inspiratory chamber to actuate the poppet valve, and the poppet valve may remain in the closed position for a greater proportion of time during a breath cycle.

In one embodiment, the breath chamber assembly further comprises a pressure control valve in fluid communication with the expiratory chamber, the pressure control valve being configured to open and release the expired air from the expiratory chamber when a pressure in the expiratory chamber exceeds a threshold pressure, and to close when the pressure in the expiratory chamber is at or below the threshold pressure. Preferably, the pressure control valve operates to maintain the pressure in the expiratory chamber at or below the threshold pressure, so as to reduce or discomfort during use. In one embodiment, the breath chamber assembly further comprises a second control valve in fluid communication with the inspiratory chamber, the second pressure control valve being configured to open and release the inhalation air from the inspiratory chamber when a pressure in the inspiratory chamber exceeds a threshold pressure, and to close when the pressure in the inspiratory chamber is at or below the threshold pressure.

In one embodiment, the pressure control valve comprises a generally tubular housing having an inwardly extending valve seat along a length thereof, first and second magnets oriented in the housing to have an attractive force therebetween, and a stop plug coupled to the first magnet, the stop plug and the first magnet being biased towards a seated fluid sealing engagement with the valve seat, and the second magnet being distanced from the first magnet and the stop plug with the valve seat interposed therebetween, wherein the second magnet is positioned to permit the first magnet and the stop plug to be in the seated fluid sealing engagement with the valve seat when the expiratory chamber is at or below the threshold pressure, and to move away from the valve seat to release the expired air when the threshold pressure is exceeded in the expiratory chamber. It has been appreciated that the pressure control valve may permit for a more gradual adjustment of the expiratory chamber pressure near the threshold pressure, in proportion to the pressure or force required to overcome the attractive magnetic force between the first and second magnets at different distances therebetween. It has been appreciated that the pressure control valve with the first and second magnets may permit a more gradual opening and closing of the valve at or near the threshold pressure, and thus more controlled regulation of the expiratory chamber pressure.

In one embodiment, a distance between the first and second magnets are adjustable to select the threshold pressure, the air outlet is adjustable to select a rate at which the expired air is released from the expiratory chamber, and at least one of the flexible partition and wall are adjustable to select a rate of pressurization in the expiratory chamber during said expiration.

In one embodiment, the device is exclusively breath powered, and the expiratory and inspiratory chambers are configured to increase the airway pressure at least at the end of said expiration and the beginning of said inspiration, and the expiratory and inspiratory chambers are depressurized to a baseline pressure at the end of said inspiration.

In yet another aspect, the present invention provides a method of providing breath powered positive airway pressure, the method comprising: a) providing a breath powered positive airway pressure device comprising an airway connector assembly for communicating air to and from a user, and a breath chamber assembly in fluid communication with the airway connector assembly, the breath chamber assembly being for increasing airway pressure during expiration and inspiration, wherein the breath chamber assembly comprises an expiratory chamber for receiving expired air from the user, an inspiratory chamber for holding inhalation air to be inspired by the user, and a resiliently flexible partition separating the expiratefy-inspiratory and expiratory chambers, the inspiratory chamber having a resiliently flexible wall configured to expand outwardly during said expiration, and the airway connector assembly comprises an airway connector for directing the expired air from and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector, wherein the breath chamber assembly further comprises: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough; and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet; b) expiring into the airway connector, whereby the flexible partition expands into and pressurizes the inspiratory chamber, and the flexible wall expands outwardly, thereby actuating the pneumatic valve to the closed position, and pressurizing the expiratory chamber; and c) inspiring the inhalation air held in the pressurized inspiratory chamber through the airway connector, whereby the inspiratory chamber is depressurized, thereby moving the pneumatic valve to the open position to permit the expired air in the expiratory chamber to be released through the air outlet.

BRIEF DESCRIPTION OF THE DRAWINGS

Further aspects and advantages of the invention will appear from the following description taken together with the accompanying drawings, in which.

DETAILED DESCRIPTION OF THE DRAWINGS

Figure 1:
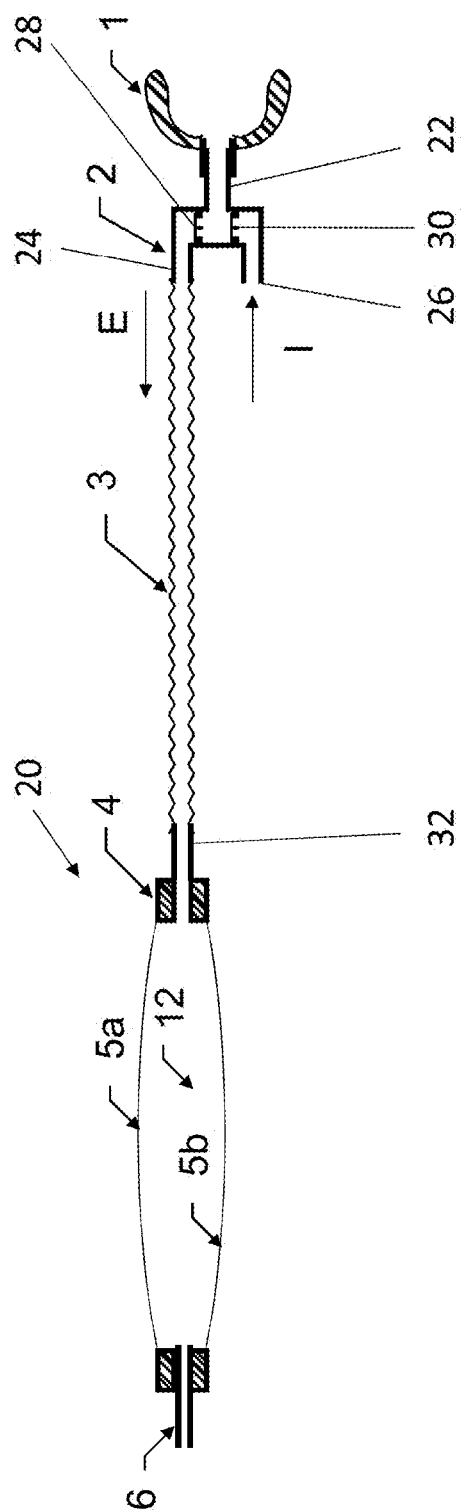
FIG. 1 shows a schematic cross-sectional view of a positive airway pressure device in accordance with a first preferred embodiment of the invention.

FIG. 1 shows a positive airway pressure device 20 in accordance with a first preferred embodiment of the invention. The device 20 includes an airway connector 1 for conveying air to and from a user's airway, a non-rebreathing valve assembly 2 in fluid communication with the airway connector 1, and a corrugated hose 3 attaching the non-rebreathing valve 2 to an expiratory chamber 12.

The airway connector 1 preferably forms a relatively fluid tight seal around the user's nose and/or mouth, so that most or all of the air that is inhaled and exhaled by the user passes therethrough. The airway connector 1 may, for example, be in the form of a nasal pillow or mask.

The non-rebreathing valve assembly 2 has an airway port 22 that connects to the airway connector 1; an expiration port 24 that connects to the corrugated hose 3; and an inspiration port 26 that is open to the external environment. A one-way expiration valve 28 is interposed between the airway port 22 and the expiration port 24; and a one-way inspiration valve 30 is interposed between the airway port 22 and the inspiration port 26. The one-way expiration valve 28 is configured to allow air to pass from the airway port 22 to the expiration port 24, and to prevent air from passing from the expiration port 24 to the airway port 22. The one-way inspiration valve 30 is configured to allow air to pass from the inspiration port 26 to the airway port 22, and to prevent air from passing from the airway port 22 to the inspiration port 26. This arrangement ensures that all of the user's expired air passes through the expiration port 24 and into the expiratory chamber 12, and all of the user's inspired air is drawn from the external environment via the inspiration port 26. The flow direction of the expired air exiting the non-rebreathing valve assembly 2 and the inspired air entering the non-rebreathing valve assembly 2 are depicted in FIG. 1 by arrows labelled as E and I, respectively.

The corrugated hose 3 provides a conduit for delivering the expired air from the expiration port 24 to the expiratory chamber 12. The corrugated hose 3 is flexible and stretchable, so as to permit the user to move relative to the expiratory chamber 12 while using the device 20.

The expiratory chamber 12 is defined by an annular frame 4 with two resiliently flexible membranes 5a, 5b stretched across each side of the frame 4. An expired air inlet 32 connects the expiratory chamber 12 to the corrugated hose 3, and an expired air outlet 6 releases the expired air into the external environment. The expired air outlet 6 provides a relatively narrow conduit, so that, during expiration, expired air is released from the expired air outlet 6 more slowly than it is received by the expired air inlet 32. This causes the expired air to collect within the expiratory chamber 12 during expiration, so that the pressure within the chamber 12 increases.

To moderate this pressure increase, the resiliently flexible membranes 5a, 5b are configured to expand or bulge outwards as the expired air collects within the chamber 12. This increases the volume of the chamber 12, so that the pressure within the chamber 12 increases more gradually than it otherwise would if the volume remained fixed. The resilient or elastic properties of the membranes 5a, 5b cause them to return to their flat, unexpanded state as the pressure within the chamber 12 returns to equilibrium with the outside environment.

The device 20 is configured so that the user is able to breathe comfortably, with breathing parameters such as tidal volume, pressure and flow rate that are clinically acceptable. For example, the size of the expiratory chamber 12, the flexibility of the membranes 5a, 5b, and the diameters of the expired air inlet 32 and the expired air outlet 6 are selected so that an acceptable volume of air can be expired therethrough at an acceptable flow rate, without requiring excessive breathing effort.

Optionally, various components of the device 20 can be made adjustable, so that the device 20 can be optimized to suit the particular clinical needs and comfort preferences of each individual user. For example, an adjustment mechanism could be used to tighten or loosen the membranes 5a, 5b, so as to alter the rate at which the pressure within the chamber 12 increases during expiration. The expired air outlet 6 could also be made adjustable, to control the rate at which the expired air is released therefrom.

To operate the device 20, the airway connector 1 is sealed against the user's nose and/or mouth. Any desired mechanism can be used to hold the connector 1 in place, such as a strap or adhesive. The user then breathes through the connector 1. During inspiration, air is drawn from the environment via the inspiration port 26 of the non-rebreathing valve assembly 2. The one-way expiration valve 28 prevents the user from inspiring air from the expiratory chamber 12. During expiration, the expired air is directed through the non-rebreathing valve assembly 2 and the corrugated hose 3 into the expiratory chamber 12. The one-way inspiration valve 30 prevents the expired air from exiting the device 20 through the inspiration port 26.

As the expired collects within the chamber 12, the membranes 5a, 5b expand outwardly, increasing the volume of the chamber 12. This causes the pressure within the chamber 12 to rise gradually during expiration. The increased pressure within the chamber 12 during expiration provides positive pressure to the patient's airway. This positive airway pressure may be used, for example, to treat obstructive sleep apnea.

During inspiration, at least some of the expired air is released from the expiratory chamber 12 via the expired air outlet 6, reducing the pressure within the chamber 12. The rate at which the expired air is released from the expired air outlet 6 may be selected so that, during a normal breathing cycle, the pressure within the chamber 12 returns to equilibrium with the external environment prior to the commencement of each expiration. Alternatively, the device 20 could be configured so that, during a normal breathing cycle, the chamber 12 does not reach equilibrium with the external environment prior to the commencement of each expiration, but rather maintains a baseline positive pressure. When configured in this way, the device 20 is able to provide at least some positive airway pressure at the very beginning of the user's expiration.

The inventor has appreciated that the device 20 is able to provide positive airway pressure during expiration, without requiring an external power source. The device 20 can also be configured to provide a gradual increase in pressure during expiration, so that the user can breathe comfortably while using the device 20.

Figure 2:
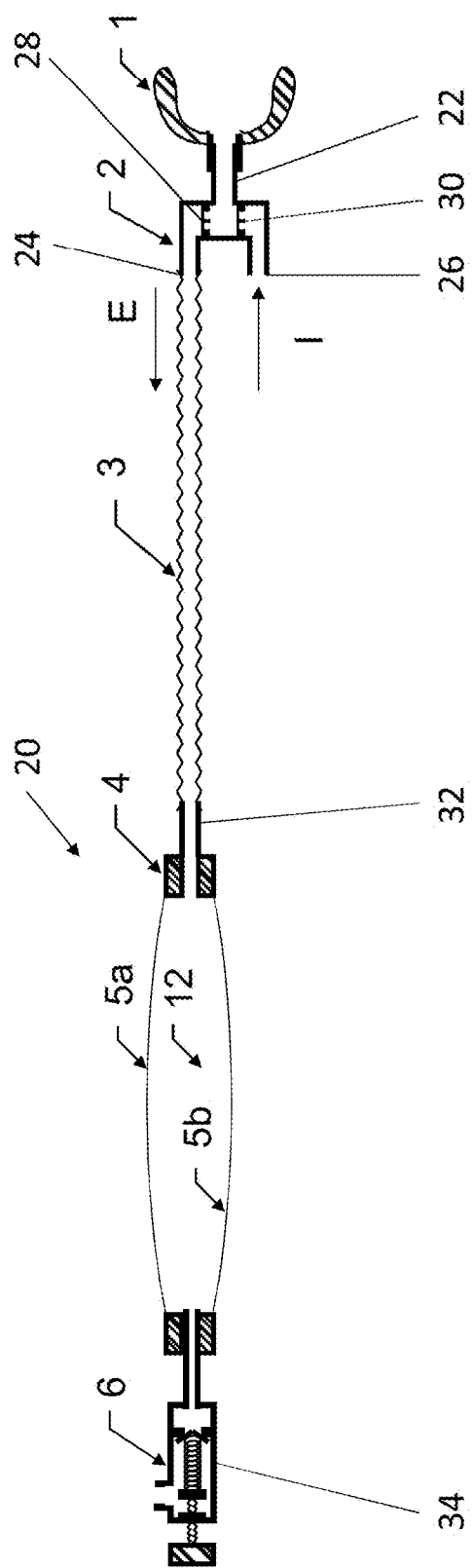
FIG. 2 shows a schematic cross-sectional view of a positive airway pressure device in accordance with a second preferred embodiment of the invention.

A positive airway pressure device 20 in accordance with a second preferred embodiment of the invention is shown in FIG. 2, wherein like numerals are used to denote like components. The device 20 shown in FIG. 2 is identical to the embodiment shown in FIG. 1, with the exception that the expired air outlet 6 now includes an adjustable pressure control valve 34. The pressure control valve 34 is configured to open, to release expired air from the chamber 12, when the pressure within the chamber 12 exceeds a preselected threshold pressure. When the pressure within the chamber 12 is at or below the threshold pressure, the pressure control valve 34 closes.

In this embodiment of the invention, the pressure control valve 34 can be used to control the pressure within the chamber 12. As the pressure control valve 34 provides the only opening through which the expired air is able to exit the expiratory chamber 12, once the chamber 12 is initially pressurized by the user's first expiration, the pressure within the chamber 12 will thereafter remain positive. This configuration of the device 20 ensures that at least a minimum positive airway pressure is provided during the user's entire expiration.

Optionally, the expired air outlet 6 can be configured so that, while the pressure control valve 34 is open, the expired air is released from the chamber 12 more slowly than it is received by the expired air inlet 32, with the result that pressure within the chamber 12 rises above the threshold pressure during expiration. During inspiration, expired air would be released from the chamber 12 until the threshold pressure was reached, at which point the pressure control valve 34 would close. This would allow the device 20 to provide a gradual increase in pressure, similar to the first embodiment described above, while also maintaining a minimum positive airway pressure at the beginning of expiration.

Alternatively, the expired air outlet 6 could be configured to release expired air from the chamber 12 very quickly when the pressure control valve 34 opens. This would prevent the pressure within the chamber 12 from rising significantly above the threshold pressure during normal expiration. This configuration would allow the device 20 to provide a relatively uniform positive airway pressure during expiration.

The pressure control valve 34 is adjustable so as to allow the user, or the user's healthcare professional, to select the threshold pressure at which the valve 34 opens. Optionally, the valve 34 is also adjustable to select the rate at which the expired air is released when the valve 34 is open. By adjusting these parameters, the device 20 can be configured in accordance with each individual user's comfort preferences and/or clinical needs.

Figure 3:
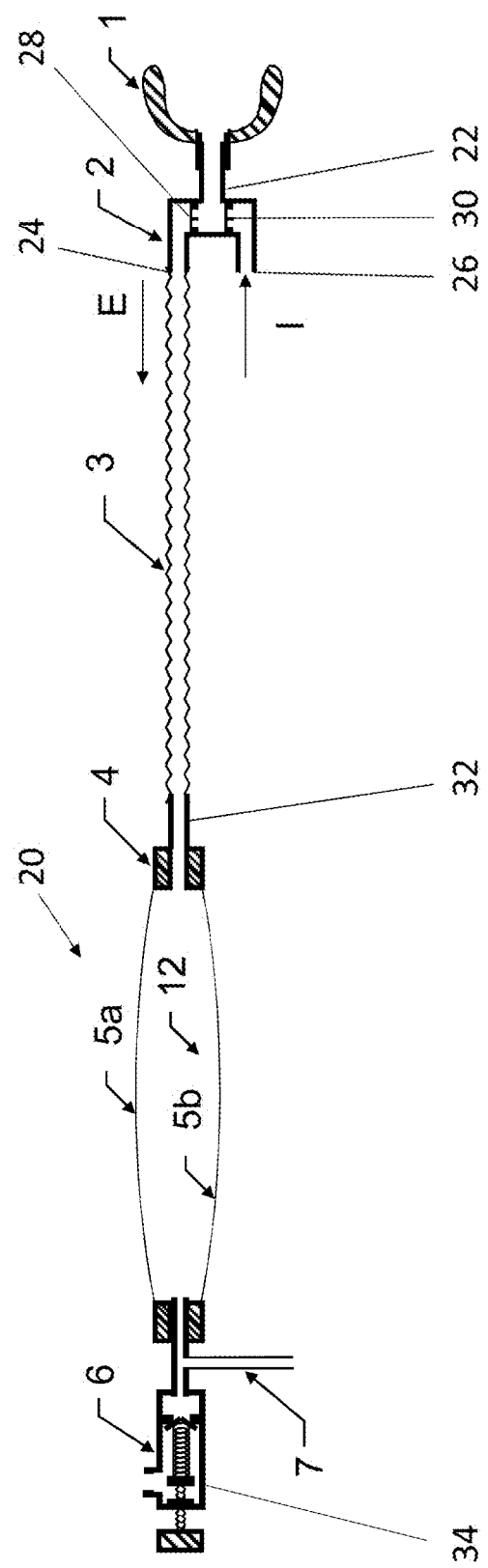
FIG. 3 shows a schematic cross-sectional view of a positive airway pressure device in accordance with a third preferred embodiment of the invention.

A positive airway pressure device 20 in accordance with a third preferred embodiment of the invention is shown in FIG. 3, wherein like numerals are used to denote like components. The device 20 shown in FIG. 3 is identical to the embodiment shown in FIG. 2, with the exception that the expired air outlet 6 additionally includes a leak tube 7, which is located between the chamber 12 and the pressure control valve 34.

The leak tube 7 permits expired air to exit the chamber 12, even when the pressure control valve 34 is closed. In this configuration, the pressure control valve 34 is used to set a maximum pressure within the chamber 12. In particular, the pressure control valve 34 can be configured to rapidly release expired air from the chamber 12 when the threshold pressure is reached, thereby preventing the pressure within the chamber 12 from rising significantly above the threshold pressure. The leak tube 7 is configured to release expired air from the chamber 12 more slowly.

This configuration allows the device 20 to provide a gradual rise in pressure during expiration, similar to the first embodiment, while also setting a maximum pressure. By setting a maximum pressure, it is possible to avoid applying excessive positive pressure to the user's airway, which could cause discomfort or otherwise interfere with normal breathing. As in the previously described embodiment, the valve 34 is adjustable so that the user, or the user's healthcare professional, can set the threshold pressure as desired.

Figure 4:
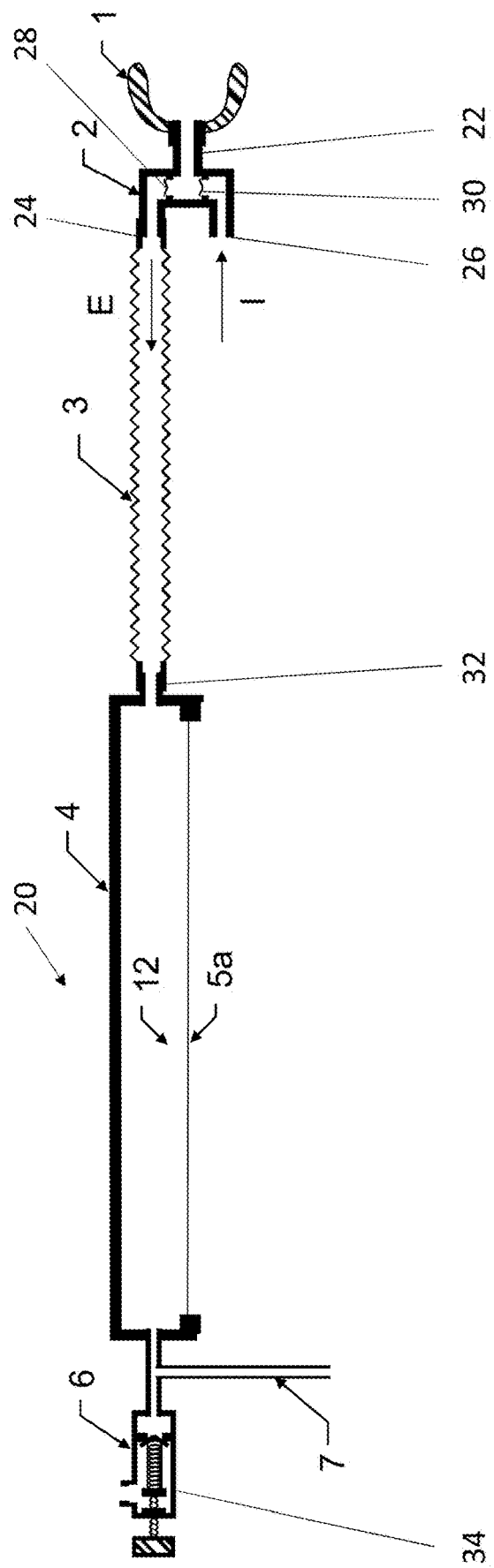
FIG. 4 shows a schematic cross-sectional view of a positive airway pressure device in accordance with a fourth preferred embodiment of the invention.

A positive airway pressure device 20 in accordance with a fourth preferred embodiment of the invention is shown in FIG. 4, wherein like numerals are used to denote like components. The device 20 shown in FIG. 4 is generally identical to the embodiment shown in FIG. 3, with the exception that one side of the frame 4 is provided with a rigid side wall, in place of the resiliently flexible membrane 5b. This flat, rigid surface makes it easier to stably rest the chamber 12 on a bedside table or the like when in use. Otherwise, the device 20 operates in an identical manner to the third embodiment as described above.

Figure 5:
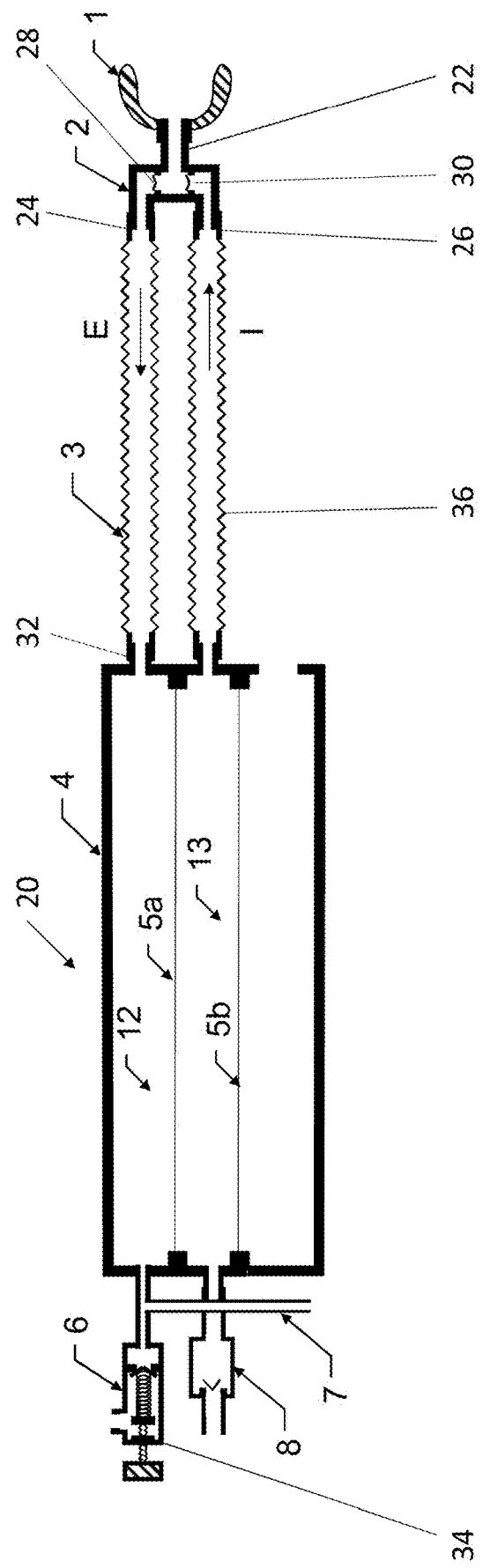
FIG. 5 shows a schematic cross-sectional view of a positive airway pressure device in accordance with a fifth preferred embodiment of the invention, showing an expiratory chamber and an inspiratory chamber in a depressurized state.
Figure 6:
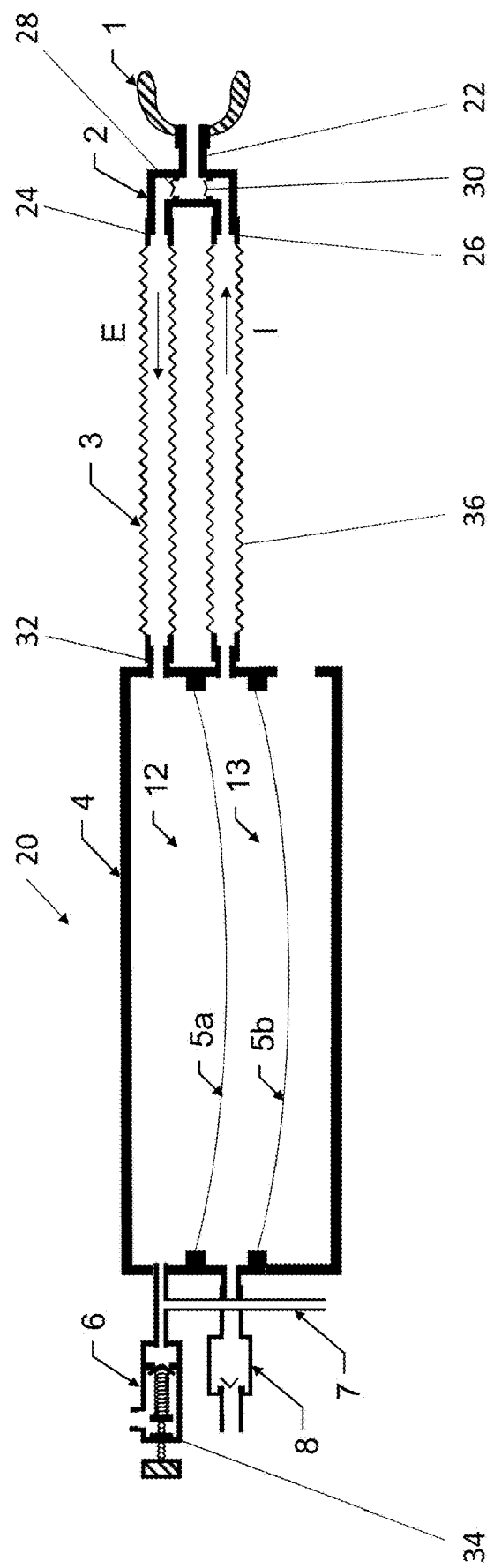
FIG. 6 shows a schematic cross-sectional view of the positive airway pressure device of FIG. 5, showing the expiratory chamber and the inspiratory chamber in a pressurized state.

A positive airway pressure device 20 in accordance with a fifth preferred embodiment of the invention is shown in FIGS. 5 and 6, wherein like numerals are used to denote like components. In this embodiment of the device 20, the frame 4 is in the form of a short, rigid cylinder, with the expiratory chamber 12 defined between the resiliently flexible membrane 5a and a side wall of the frame 4.

The frame 4 also contains an inspiratory chamber 13 for holding air to be inspired by the user. The inspiratory chamber 13 is defined between the resiliently flexible membrane 5a and the resiliently flexible membrane 5b, and is connected to the inspiration port 26 by a second corrugated hose 36. The inspiratory chamber 13 receives the air to be inspired from the external environment via a low resistance one-way air inlet valve 8.

As in the previously described embodiments, to operate the device 20, the user breathes through the airway connector 1. The expired air is directed through the non-rebreathing valve assembly 2 and the corrugated hose 3 into the expiratory chamber 12. The leak tube 7 is configured to release expired air from the chamber 12 more slowly than it is received by the expired air inlet 32, such that the pressure within the chamber 12 increases during expiration.

As in the previously described embodiments, the flexible membrane 5a expands outward to increase the volume of the expiratory chamber 12 and accommodate the expired air that is received, as shown in FIG. 6. However, unlike in the previously described embodiments, in this embodiment the flexible membrane 5a forms a partition between the expiratory chamber 12 and the inspiratory chamber 13, such that the flexible membrane 5a also expands into the inspiratory chamber 13, decreasing the volume thereof. This causes the pressure in both the expiratory chamber 12 and the inspiratory chamber 13 to increase.

As in the previously described embodiments, the pressurization of the expiratory chamber 12 provides positive airway pressure to the user during expiration. In addition, in this embodiment the pressurization of the inspiratory chamber 13 also provides positive airway pressure at least at the beginning of inspiration.

During inspiration, the user initially draws pressurized air from the inspiratory chamber 13 via the airway connector 1. As the air is drawn from the chamber 13, the pressure within the chamber 13 decreases. Once the pressure within the chamber 13 reaches the same pressure as the external environment, additional air may be drawn through the low resistance one-way air inlet valve 8.

Expired air is released from the expiratory chamber 12 via the leak tube 7 during inspiration, so that the pressure within the expiratory chamber 12 returns to a baseline level, and the flexible membrane 5a returns to its flat, unexpanded state as shown in FIG. 5. This permits the inspiratory chamber 13 to return to its initial volume before getting compressed and pressurized again during the next expiration.

Figure 7:
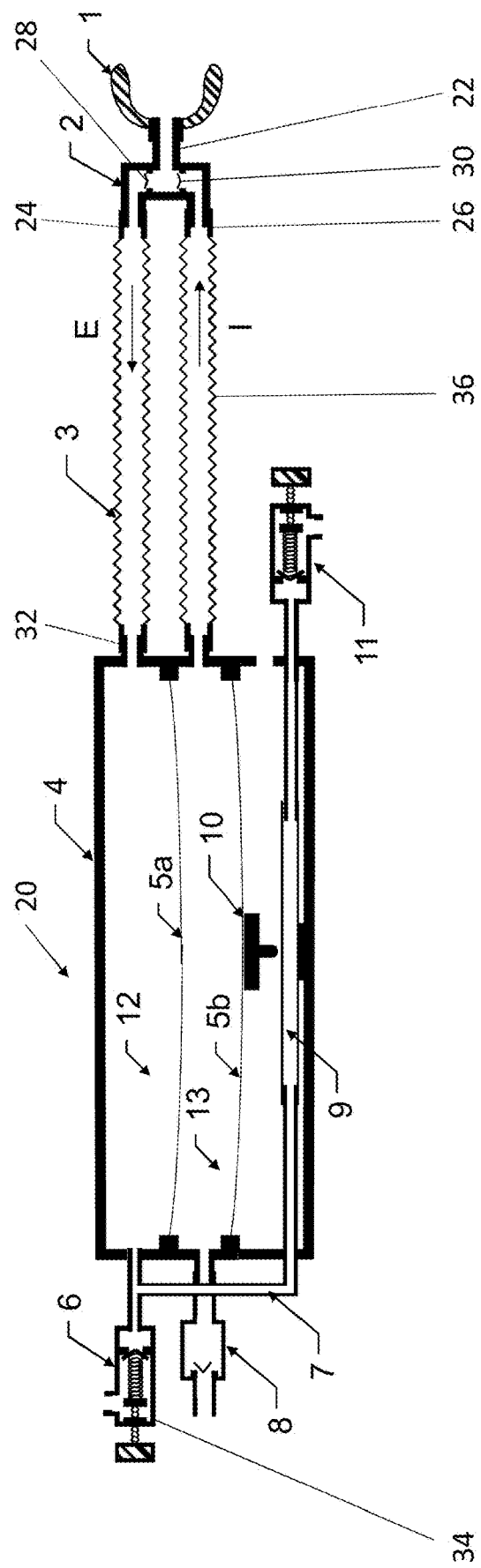
FIG. 7 shows a schematic cross-sectional view of a positive airway pressure device in accordance with a sixth preferred embodiment of the invention, showing an expiratory chamber and an inspiratory chamber in a depressurized state.
Figure 8:
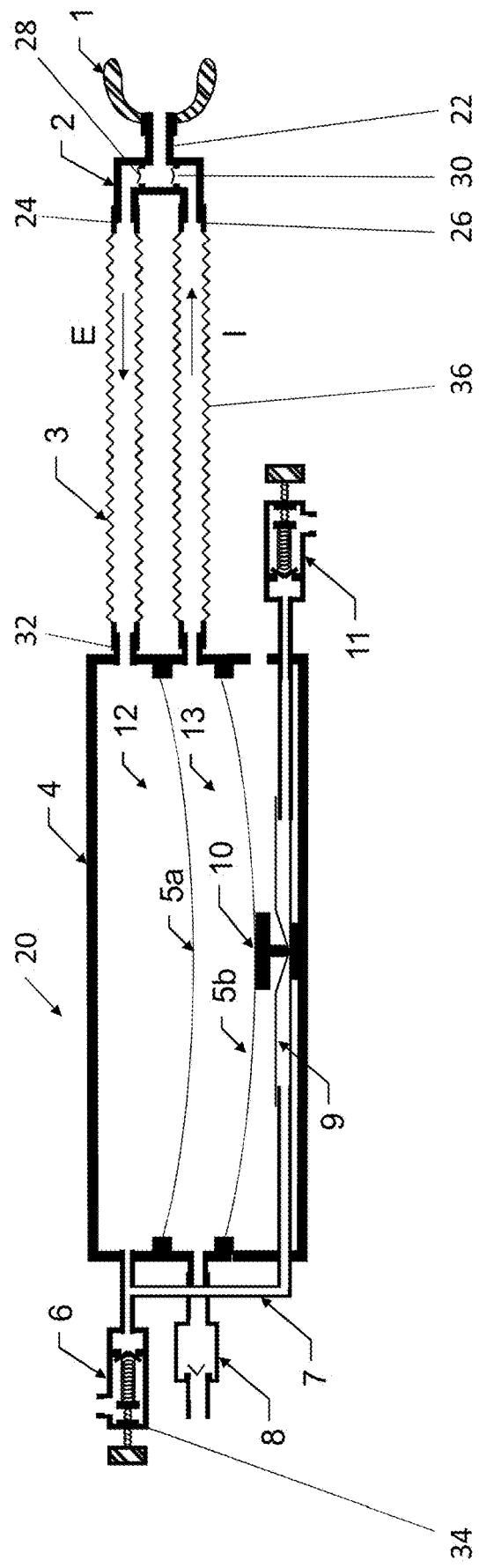
FIG. 8 shows a schematic cross-sectional view of the positive airway pressure device of FIG. 7, showing the expiratory chamber and the inspiratory chamber in a pressurized state.

A positive airway pressure device 20 in accordance with a sixth preferred embodiment of the invention is shown in FIGS. 7 and 8, wherein like numerals are used to denote like components. The device 20 shown in FIGS. 7 and 8 is generally identical to the embodiment shown in FIGS. 5 and 6, with the exception that an additional valve assembly is included for controlling the release of expired air from the expiratory chamber 12.

In this embodiment of the invention, the leak tube 7 includes a flexible section 9 positioned inside the frame 4, as well as a second pressure control valve 11. The pressure control valve 11 is used to set a minimum pressure within the expiratory chamber 12, in much the same way as in the second embodiment described above. The device 20 also includes an occluder 10, which is fixed to the bottom surface of the flexible membrane 5b.

During operation of the device 20, the user's expired air collects within the expiratory chamber 12. This causes the flexible membrane 5a to expand into the inspiratory chamber 13, pressurizing the air contained therein. The increased pressure within the chamber 13 furthermore causes the membrane 5b to expand outwardly, pushing the occluder 10 into engagement with the flexible section 9 of the leak tube 7, as shown in FIG. 8.

The engagement of the occluder 10 with the flexible section 9 closes the leak tube 7, preventing the release of expired air from the expiratory chamber 12 through the leak tube 7. This ensures that the expiratory chamber 12 and the inspiratory chamber 13 remain pressurized during the entire expiration, even if the rate at which expired air enters the expiratory chamber 12 decreases at the end of expiration. The pressure control valve 34 ensures that the pressure within the chamber 12 does not exceed a pre-selected maximum pressure, as in the previously described embodiments.

At the beginning of inspiration, the engagement of the occluder 10 with the flexible section 9 of the leak tube 7 ensures that the inspiratory chamber 13 is pressurized. As the pressurized air is drawn from the inspiratory chamber 13 through the corrugated hose 36, the pressure within the chamber 13 decreases. This causes the flexible membrane 5b to retract away from the flexible section 9, pulling the occluder 10 out of engagement with the flexible section 9. This opens the leak tube 7, allowing expired air to escape from the expiratory chamber 12, and decreasing the pressure therein. Once a baseline minimum pressure is reached, the pressure control valve 11 closes.

The device 20 is configured so that the expiratory chamber 12 reaches the minimum baseline pressure by the end of a normal inspiration, allowing the expiratory chamber 12 and the inspiratory chamber 13 to return to their baseline volumes and pressures before the next expiration begins.

Figure 9:
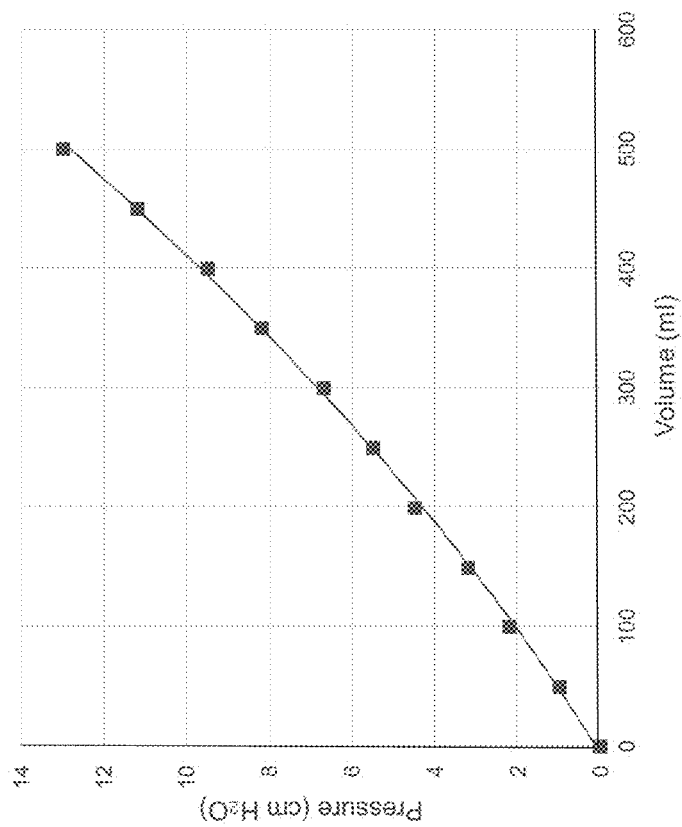
FIG. 9 shows a plot of the relationship between pressure and volume in an expiratory chamber of the device of FIG. 1.
Figure 10:
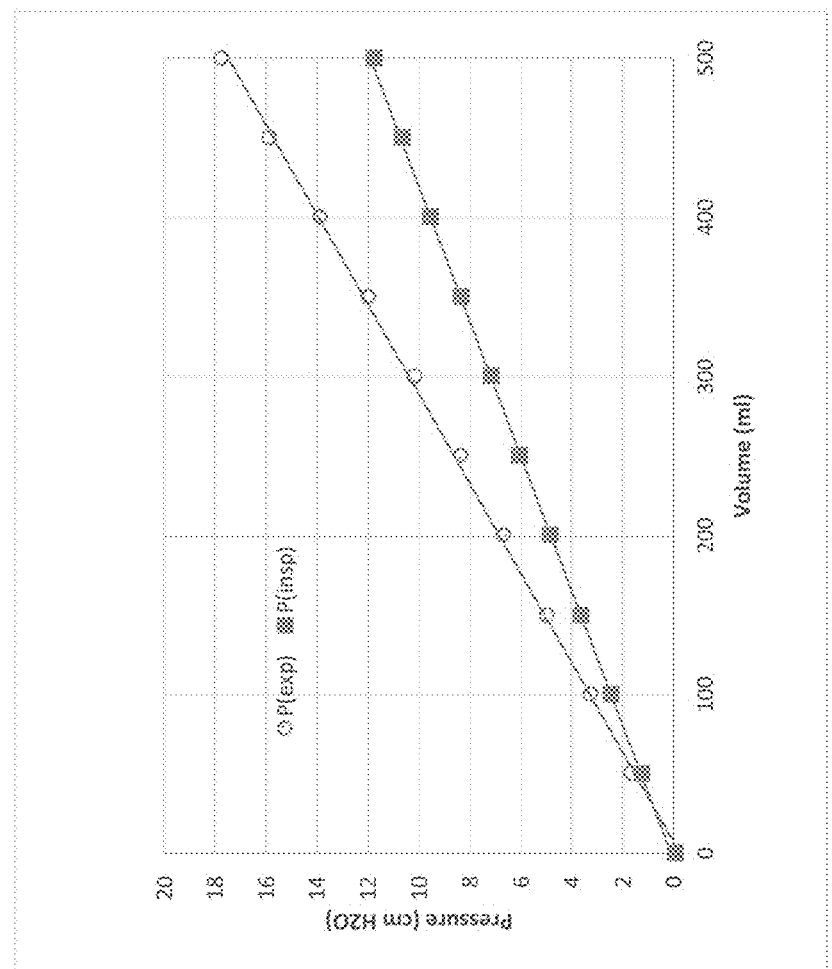
FIG. 10 shows a plot of the relationship between pressure and volume in the expiratory chamber and the inspiratory chamber of the device of FIG. 7.

The relationship between pressure and volume in the inspiratory chamber 13 and the expiratory chamber 12 is shown in FIG. 10. This curve was obtained by monitoring pressure within the chambers 12, 13 during stepwise inflation, with all outlets blocked. The relationship between pressure and volume depends on the diameter of the flexible membranes 5a, 5b and the magnitude of their stretch. In general, the larger the diameter of the membranes 5a, 5b, the smaller the incremental increase in pressure during stepwise inflation. The tighter the membranes 5a, 5b are stretched, the higher the incremental pressure rise inside the chambers 12, 13. The diameter and stretch properties of the membranes 5a, 5b may be selected or adjusted to provide the desired pressure rise in response to a normal tidal volume. The relationship between pressure and volume in the expiratory chamber 12 of the device 20 shown in FIG. 1 is depicted in FIG. 9.

In some embodiments of the invention, the chambers 12, 13 and their stretched membranes 5a, 5b may be modelled by electric capacitors. In particular, the higher the volume (charge), the higher the pressure (voltage). Furthermore, the combination of the two chambers 12 and 13 may be modelled by the series combination of two capacitors.

It will be understood that, although various features of the invention have been described with respect to one or another of the embodiments of the invention, the various features and embodiments of the invention may be combined or used in conjunction with other features and embodiments of the invention as described and illustrated herein.

Although the preferred embodiments described above show the device 20 as including a non-rebreathing valve assembly 2, it is to be appreciated that this valve assembly 2 is not strictly necessary. For example, in embodiments of the device 20 where positive airway pressure is provided only during expiration, and where the airway connector 1 interfaces only with the user's nose, the device 20 could be designed so that the user expires into the airway connector 1, and inspires directly from the external environment through the user's mouth. In such embodiments, a non-rebreathing valve assembly 2 would not be strictly required to operate the device 20.

It is to be appreciated that the device 20 need not have the specific size, shape, and configuration as shown in the exemplary embodiments. Rather, any shape or construction that provides positive airway pressure in a functionally equivalent or analogous manner could be used as desired.

The airway connector 1 could have any suitable construction for transporting air to and from the user's airway, including for example a nose pillow, a nose mask, or a full face mask. The airway connector 1 could also be adapted to interface indirectly with the user's airway. For example, for patients who breathe through a breathing tube, the airway connector 1 could be adapted to connect to the breathing tube.

Although the device 20 has been described above as receiving air to be inspired from the external environment, it is to be appreciated that the device 20 could be adapted to receive air from any desired source. For example, the device 20 could receive air from a humidifier or an oxygenated source, if desired. The device 20 could also be configured to deliver the expired air to another apparatus, rather than releasing it into the external environment. For example, the expired air could be collected by an apparatus that measures tidal volume, $O_2$ and $CO_2$ concentrations, or other parameters.

The flexible membranes 5a, 5b could be made from any suitable materials that provide the desired flexibility and resiliency, including natural and synthetic materials such as rubbers, elastomers, latex, polyisoprene, polychloroprene and the like.

The one-way inspiration valve 30, the one-way expiration valve 28, the low resistance one-way air inlet valve 8, and the pressure control valves 6 and 11 could have any desired construction suitable to provide control of air flow and/or pressure, including for example ball valves, diaphragm valves, duckbill valves, and the like. The pressure control valves 6 and 11 could include disposable or reusable positive end-expiratory pressure (PEEP) valves.

The corrugated hoses 3 and 36 could be replaced with any suitable conduits for transporting air to the expiratory chamber 12 and from the inspiratory chamber 13, including for example non-corrugated tubes with any suitable diameter, length, and degree of flexibility.

It is to be appreciated that, in some embodiments, the device 20 may incorporate features that require electricity to operate. For example, the device 20 could incorporate sensors and a display for recording and displaying information about the operation of the device 20, such as tidal volume, pressure, and other parameters. The device 20 could also incorporate a generator for converting some of the mechanical energy of the user's breathing into electricity, for powering such features.

Figure 11:
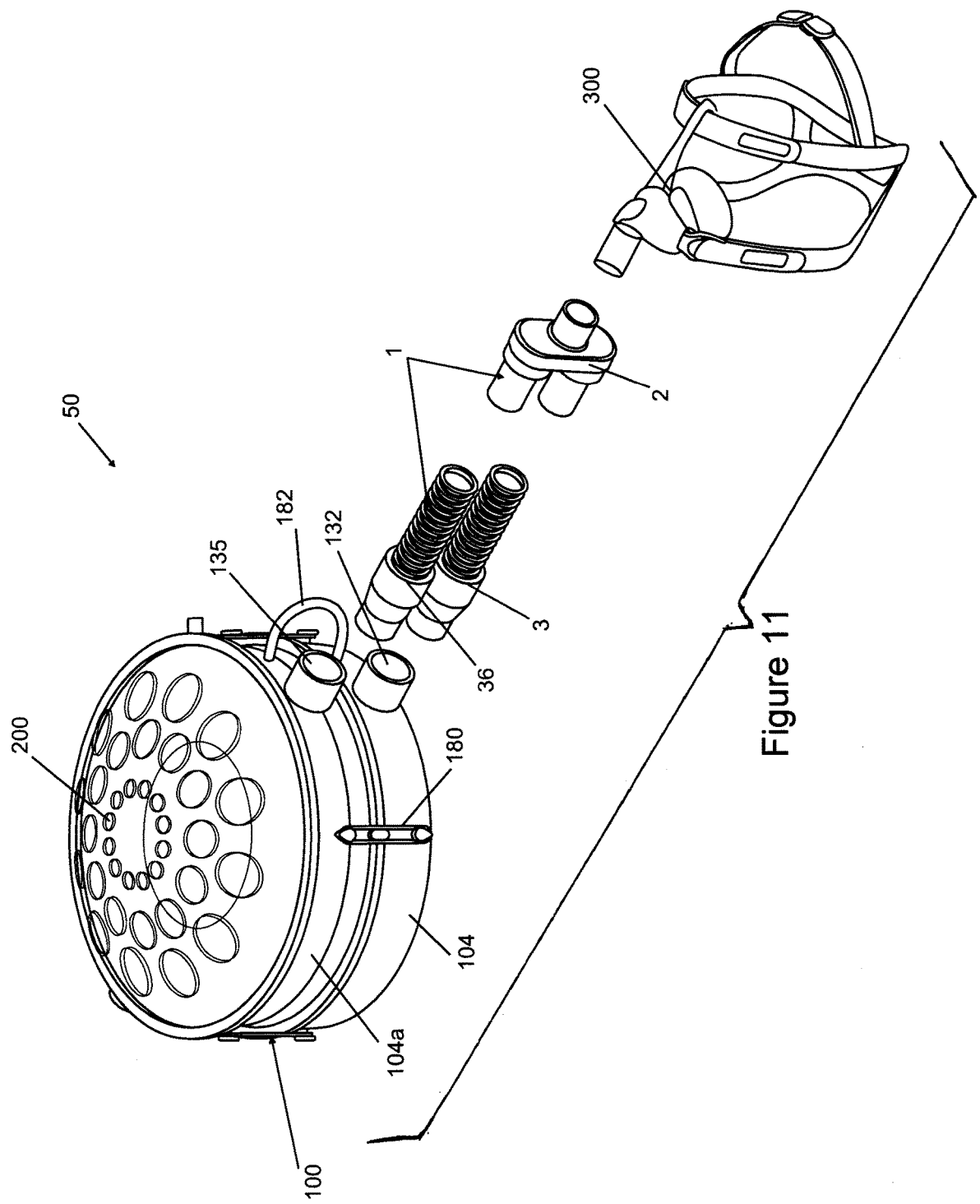
FIG. 11 shows a top perspective view of a positive airway pressure device in accordance with a preferred embodiment of the invention.
Figure 12:
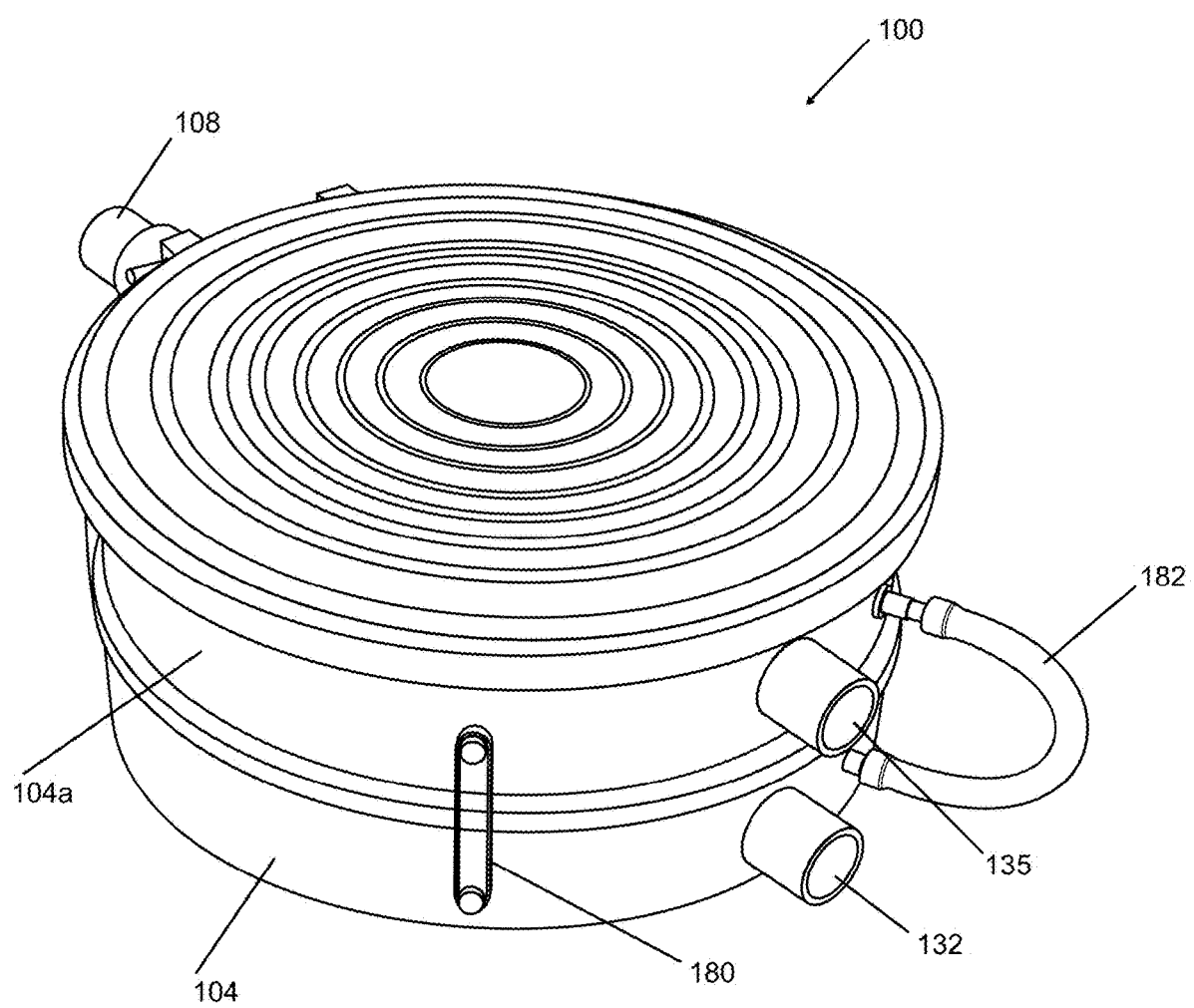
FIG. 12 shows a top perspective view of a breath chamber assembly included with the positive airway pressure device shown in FIG. 11.
Figure 13:
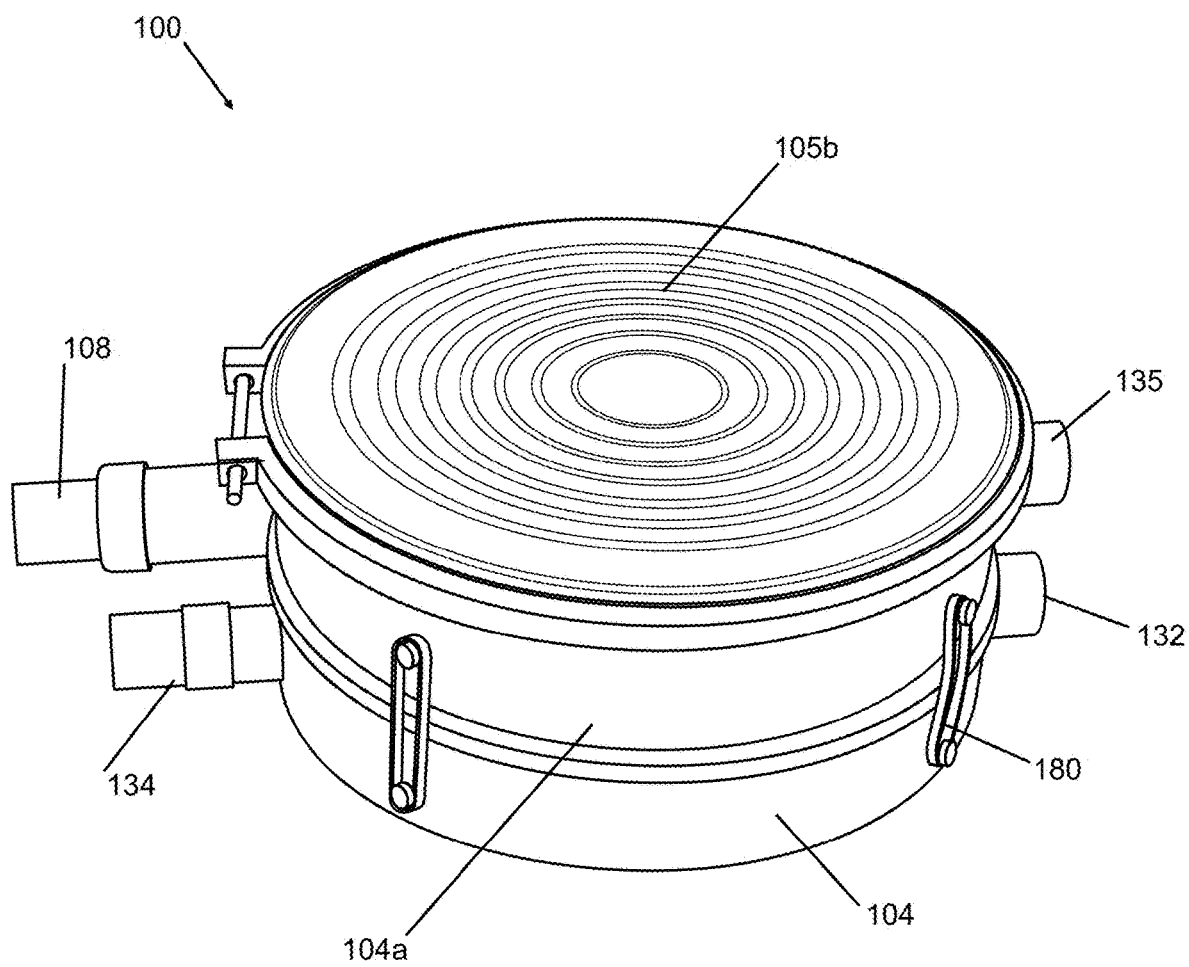
FIG. 13 shows another top perspective view of the breath chamber assembly shown in FIG. 12.
Figure 14:
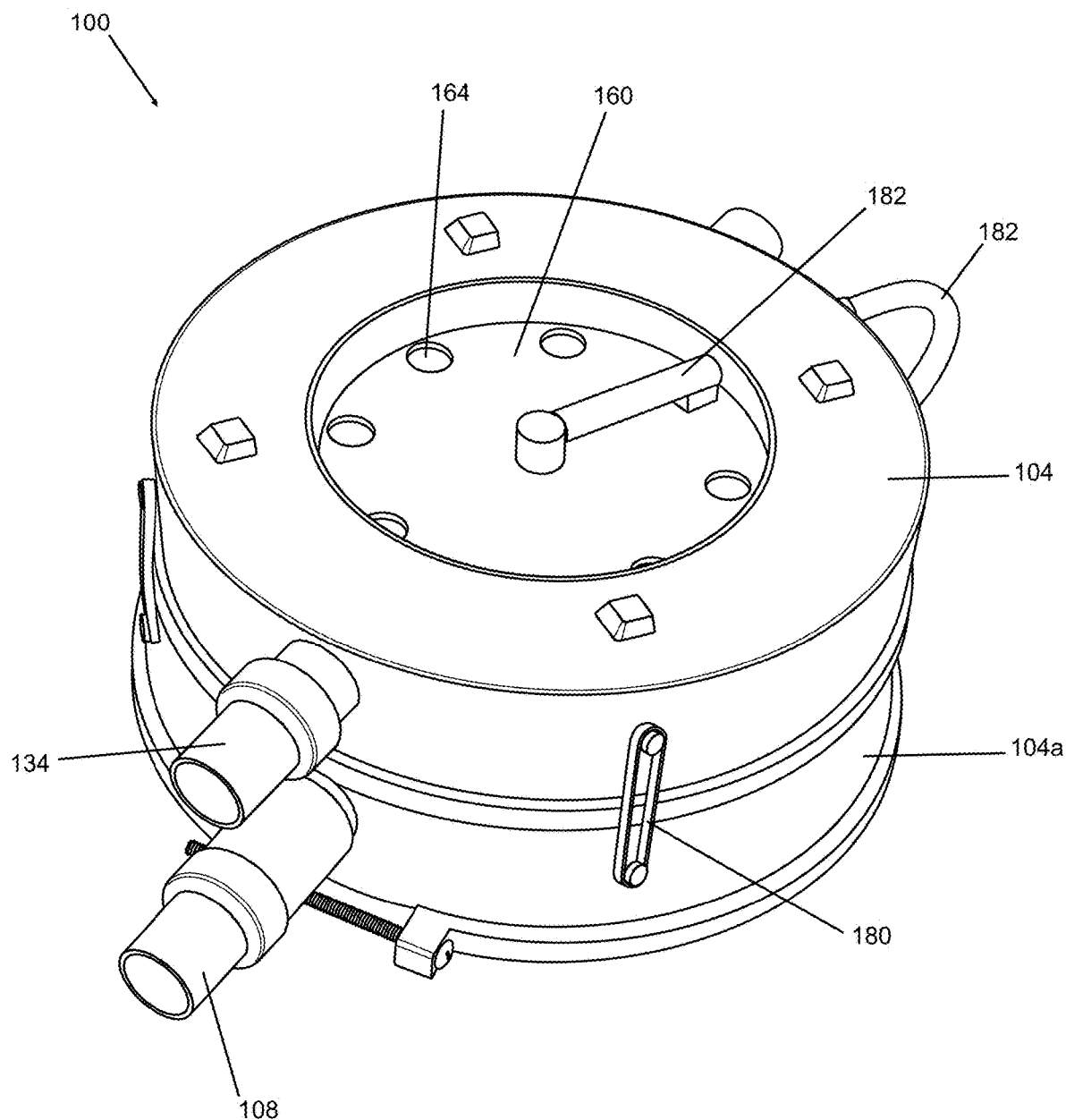
FIG. 14 shows a bottom perspective view the breath chamber assembly shown in FIG. 12.

A positive airway pressure device 50 according to another preferred embodiment of the invention is illustrated in FIG. 11 which shows a perspective view of the device 50. The device 50 includes an airway connector or airway connector assembly 1 and a breath chamber assembly 100 in fluid communication with the connector 1. The assembly 100 is shown in FIG. 11 with an optional top cover 200 and head mask 300 to be worn by the user to direct air to and from the connector 1. The device 50 shares a number of similarities with the device 20 of the fifth preferred embodiment of the invention shown in FIGS. 5 and 6, and also incorporates a number of different features.

The airway connector 1 is identical to that described above for the device 20 of the fifth and sixth embodiments shown in FIGS. 5 to 8. The connector 1 includes the non-breathing valve assembly 2 and the corrugated hoses 3, 36 fluidically connected respectively during operation to the expiratory and inspiratory chambers, as further described below.

Figure 15:
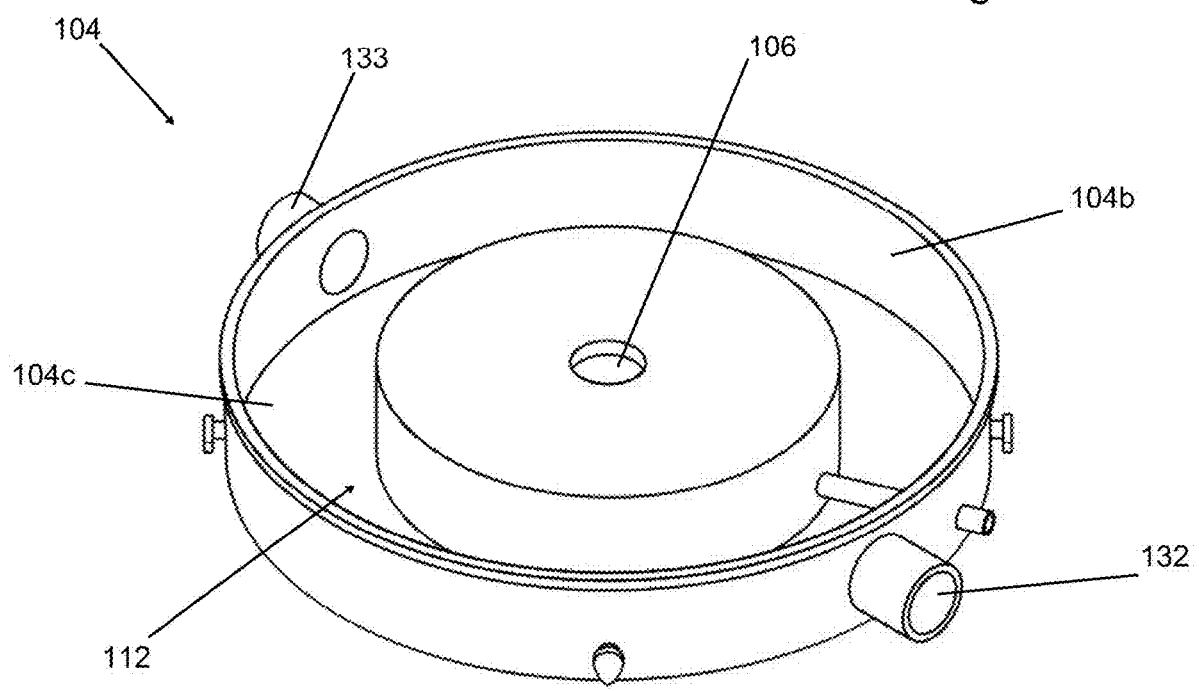
FIG. 15 shows a top perspective view of an expiratory chamber frame included with the breath chamber assembly shown in FIG. 12.
Figure 16:
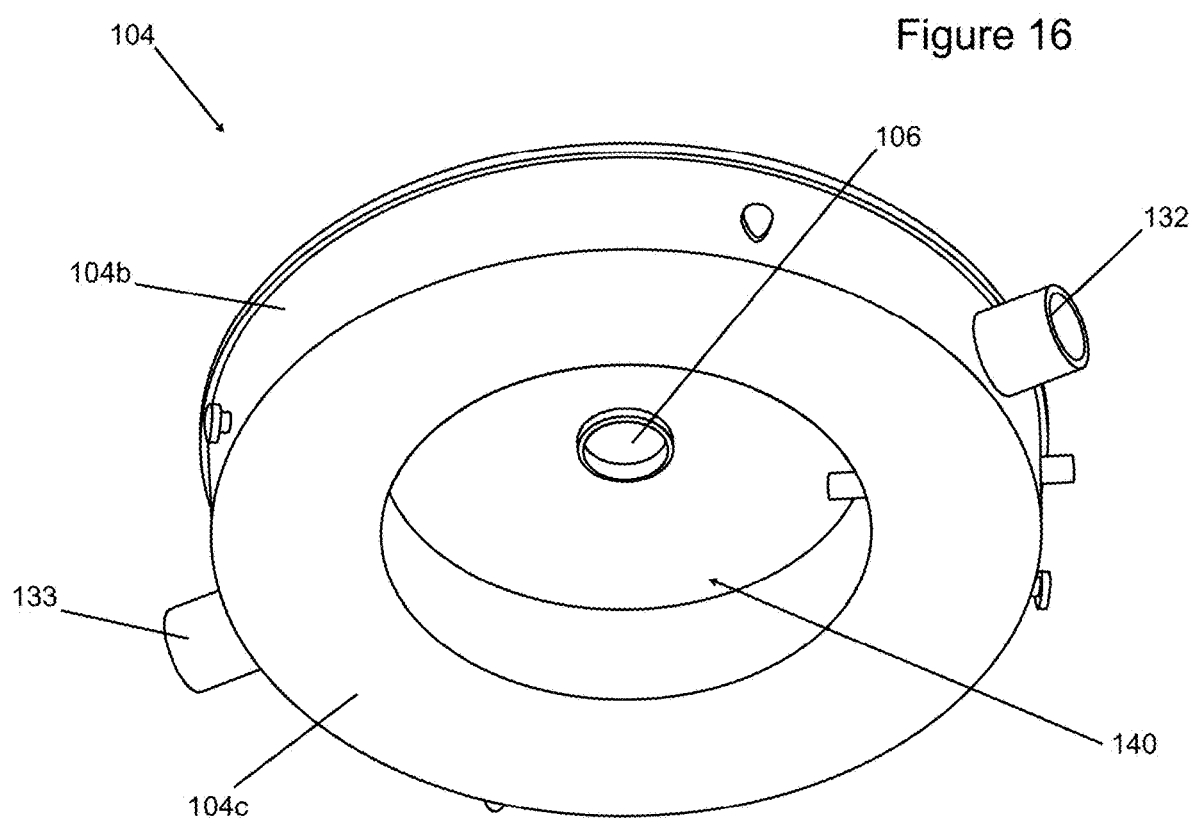
FIG. 16 shows a bottom perspective view of the expiratory chamber frame shown in FIG. 15.
Figure 20:
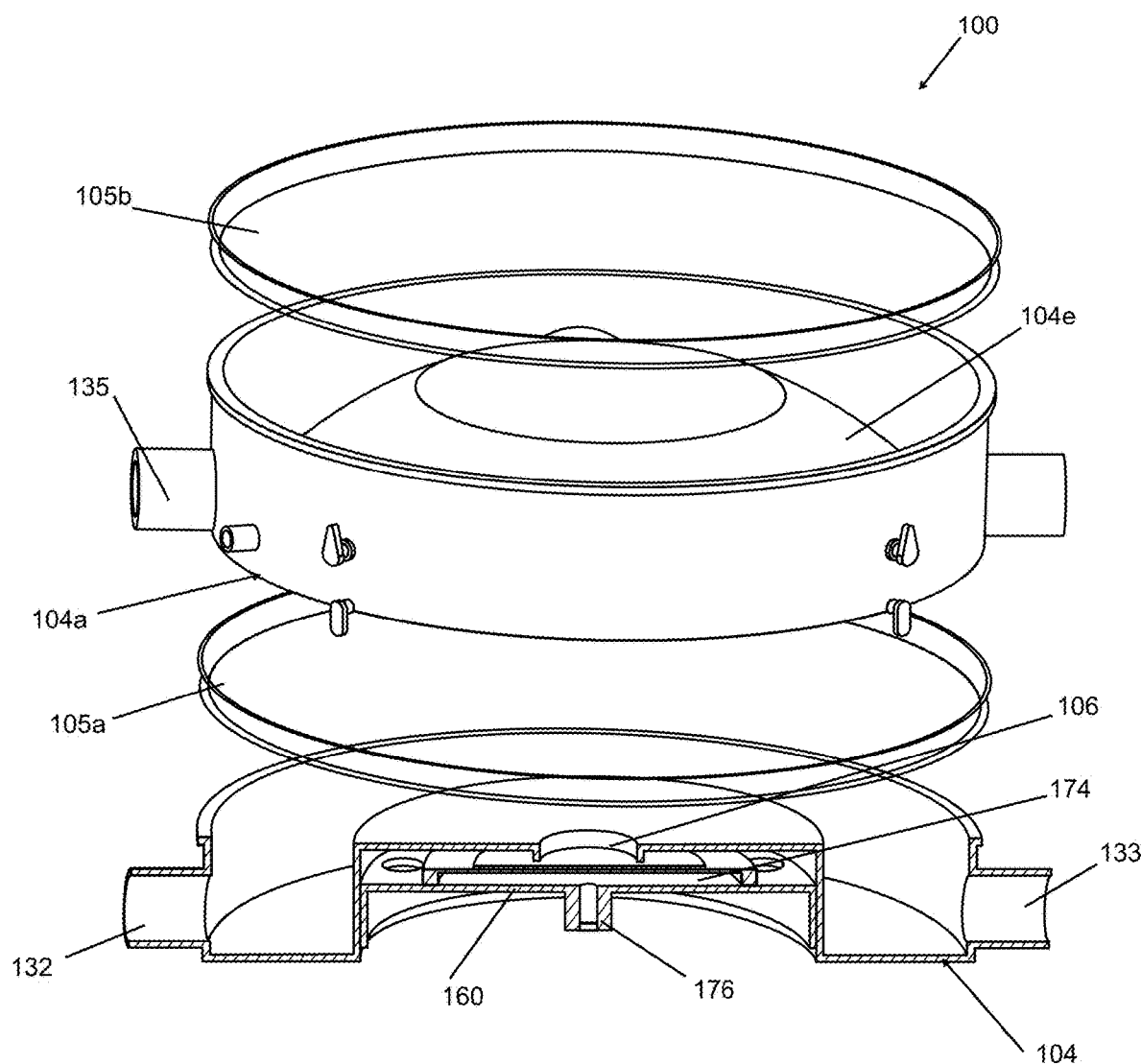
FIG. 20 shows a perspective exploded view of the breath chamber assembly shown in FIG. 12, and which includes a partial cross-sectional view of the expiratory chamber frame and the poppet valve.
Figure 21:
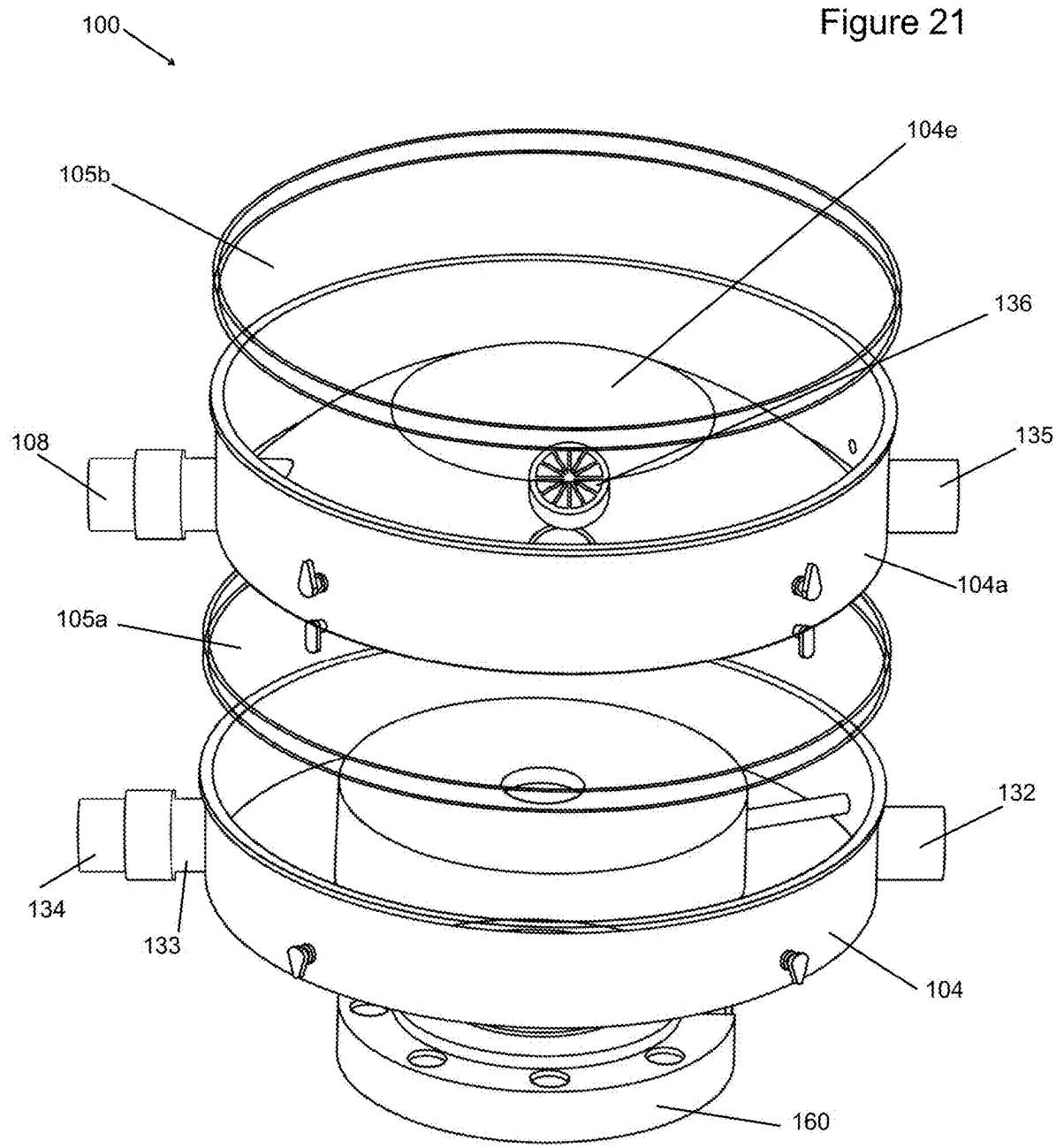
FIG. 21 shows another perspective exploded view of the breath chamber assembly shown in FIG. 12.

As shown in FIGS. 11 to 14, the breath chamber assembly 100 has generally cylindrical expiratory chamber frame 104 and inspiratory chamber frame 104a. As best seen in FIG. 15, the expiratory chamber frame 104 includes an annular sidewall 104b and a circular bottom wall 104c to cooperatively define an expiratory chamber 112 above the wall 104c. As best seen in FIG. 16, the bottom wall 104c also defines a downwardly open valve housing recess 140 opposed to the chamber 112, and an expired air outlet 106 to establish fluid communication between the chamber 112 and the recess 140. The sidewall 104b defines an expired air inlet 132 for connecting to the corrugated hose 3, and a pressure control air outlet 133 for connecting to a pressure control valve 134, as further discussed below. As best seen in FIGS. 20 and 21, the assembly 100 also has a resiliently flexible membrane or partition 105a removably coupled to an upper open end of the frame 104 to enclose the chamber 112.

Figure 17:
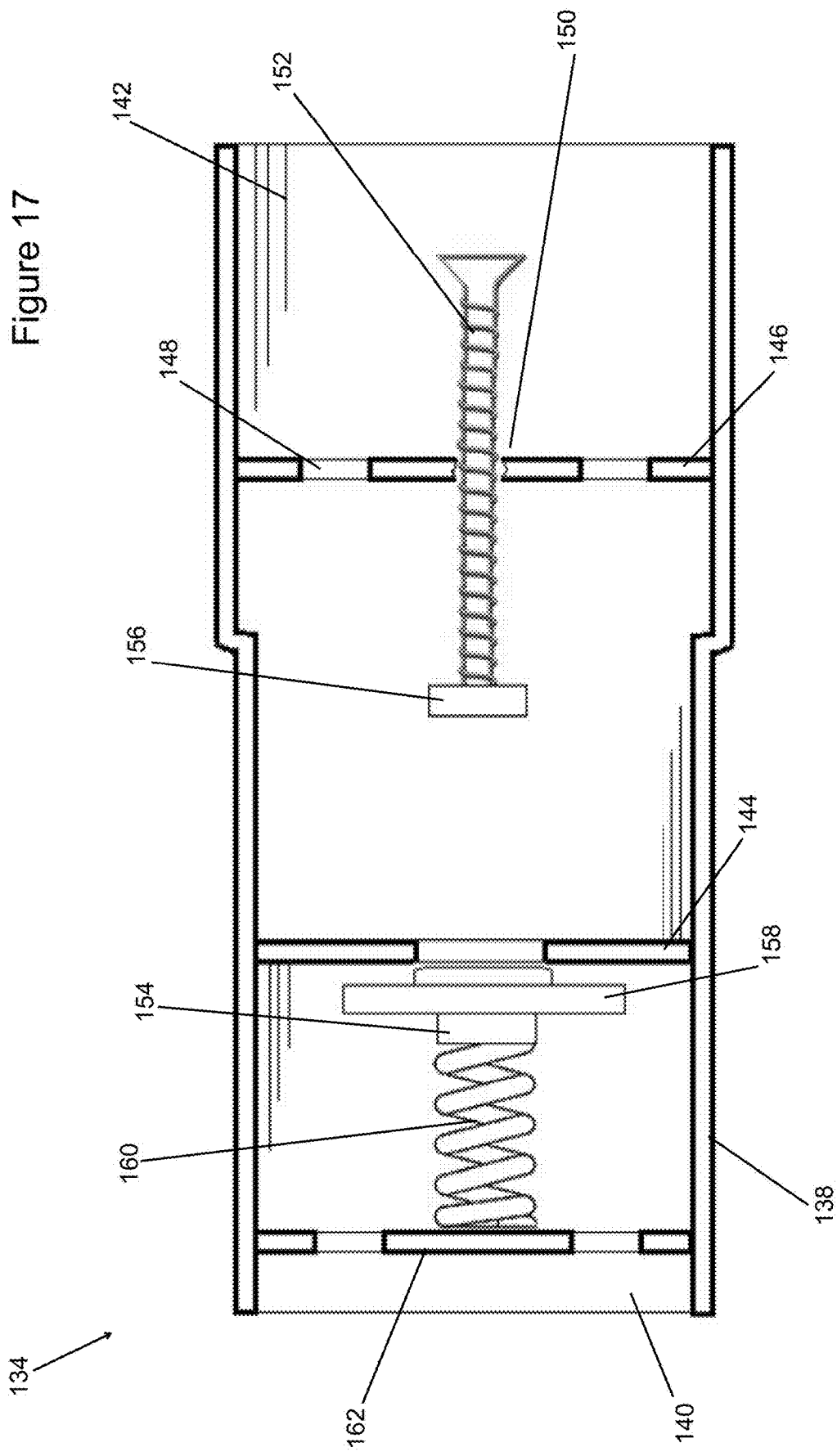
FIG. 17 shows a lateral cross-sectional view of the pressure control valve included with the breath chamber assembly shown in FIG. 12.

As best seen in FIG. 17, the pressure control valve 134 is constructed with a cylindrical valve housing 138 having a distal air release end 140 and a proximal attachment end 142, where the end 142 is sized to receive the pressure control air outlet 133 in fluid communication therewith. The housing 138 has a valve seat 144 proximal to the distal end 140 and an inwardly extending flange 146 proximal to the attachment end 142, where the flange 146 defines a number of peripheral apertures 148 for allowing air to flow therethrough. The flange 146 also defines a threaded central aperture 150 for complementary threaded engagement with a threaded magnet holding bolt 152, as further described below.

Opening and closing of the valve 134 at a preselected threshold pressure is controlled by first and second magnets 154, 156 disposed along a length of the housing 138. The first magnet 154 is coupled to a disk valve plug 158, and the magnet 154 and the plug 158 together are biased towards a seated fluid sealing engagement in the valve seat 144 by a compression spring 160. The compression spring 160 is affixed to a perforated disk 162 integrally formed within the housing 138 adjacent to the distal end 140. The valve 134 also includes the bolt 152 threadably engaged in the aperture 150, and the second magnet 156 is coupled to an axial end of the bolt 152 near the valve seat 144. The second magnet 156 is oriented and positioned on the bolt 152 relative to the first magnet 154 to provide an attractive magnetic force between the magnets 154, 156. The distance between the magnets 154, 156 is selected such that the attractive magnetic force maintains the first magnet 154 and the plug 158 in the seated engagement in the valve seat 144 at or below the threshold pressure in the expiratory chamber 112, and allow the magnet 154 and the plug 158 to move away from the valve seat 144 above the threshold pressure, as further discussed below.

Figure 18:
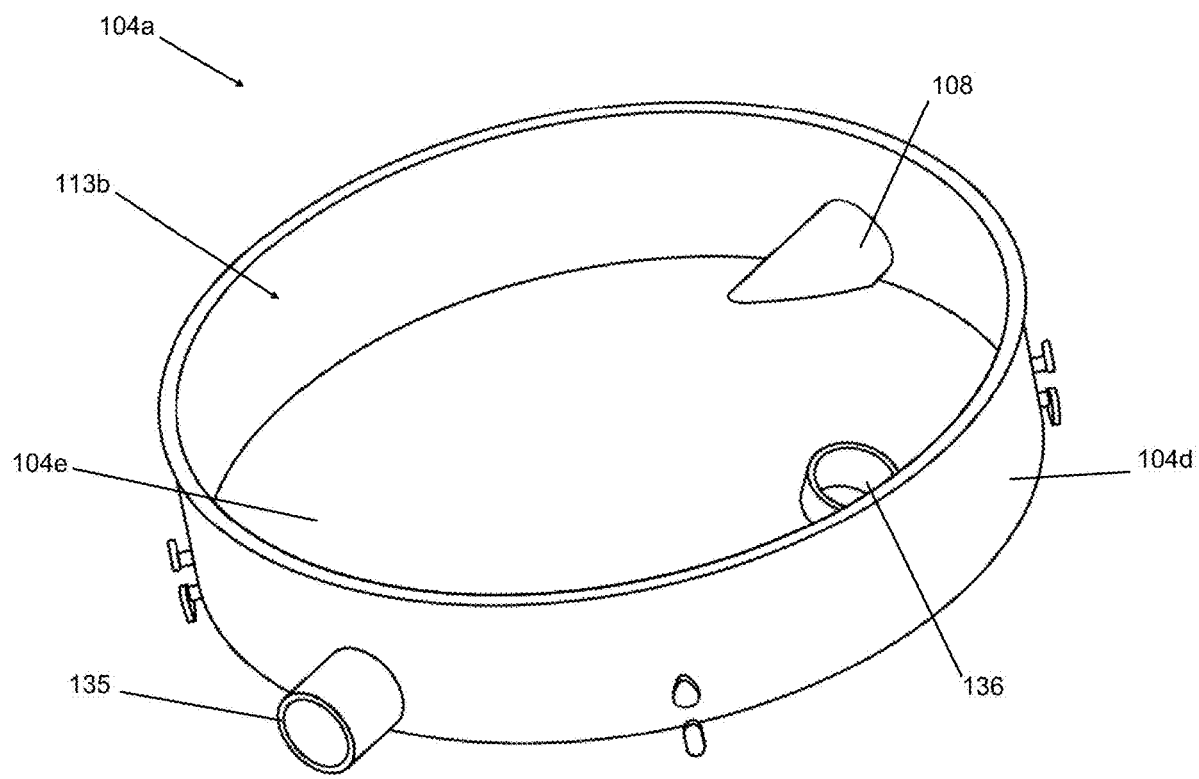
FIG. 18 shows a top perspective view of an inspiratory chamber frame included with the breath chamber assembly shown in FIG. 12.

As seen in FIG. 18, the inspiratory chamber frame 104a has an annular sidewall 104d and an internal inspiratory chamber wall 104e cooperatively defining an inspiratory chamber having divided first and second inspiratory cavities 113a, 113b (the first cavity not shown). The wall 104e has a generally dome-like shape extending upwardly into the second cavity 113b and defining the first cavity 113a below. The sidewall 104d has a low-resistance one-way air inlet valve 108 fluidically connected to the first inspiratory cavity 113a, so as to allow air from the external environment to enter into the cavity 113a. The sidewall 104d also defines an inhalation air outlet 135 for fluid communication with the corrugated hose 36, and to permit the air inside the second cavity 113b to be inspired by the user during inspiration, as further described below. The assembly 100 is further provided with a one-way inspiratory chamber valve 136 disposed in the internal wall 104e to allow movement of the inhalation air from the first cavity 113a to the second cavity 113b, and to prevent reverse air movement from the second cavity 113b to the first cavity 113a. As best seen in FIGS. 20 and 21, the assembly 100 also has a resiliently flexible membrane or wall 105b removably coupled to an upper open end of the inspiratory chamber frame 104a to enclose the second cavity 113b.

Figure 19:
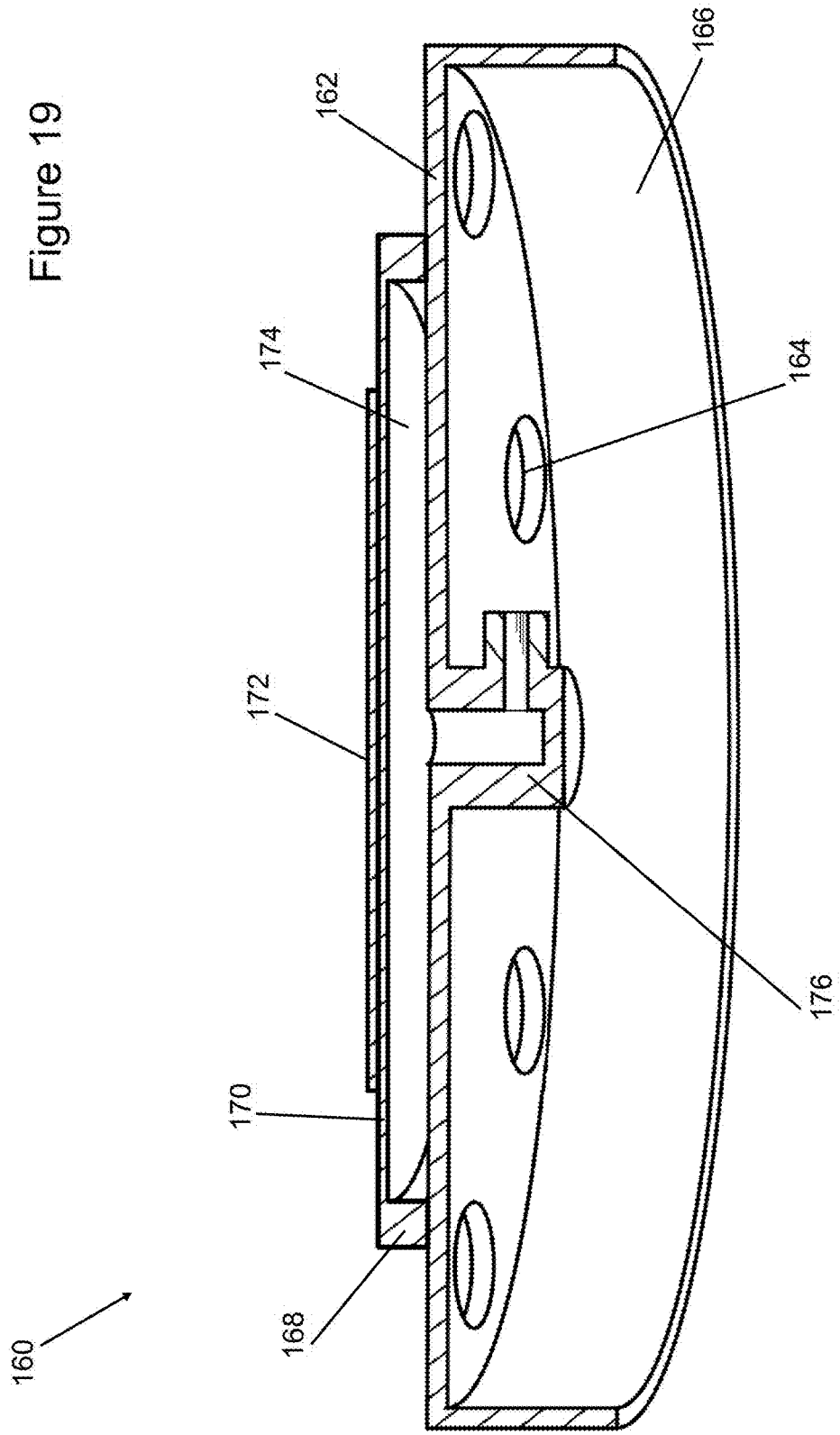
FIG. 19 shows a lateral cross-sectional view of a poppet valve included with the breath chamber assembly shown in FIG. 12.

As best seen in FIGS. 19 to 21, the assembly 100 also has a poppet or mushroom valve 160 sized to be received in the valve housing recess 140 defined by the bottom wall 104c of the expiratory chamber frame 104. The valve 160 is constructed with a perforated disk 162 having multiple peripheral bores 164, and an annular retention flange 166 extending downwardly from the outer periphery of the disk 162. The valve 160 also has an upwardly extending annular ring 168 disposed inwardly of the bores 164, and the ring 168 is coupled to an upper resiliently flexible valve membrane 170 having disposed thereon a disk plug 172. The disk 162, the ring 168 and the membrane 170 cooperatively define a valve actuator chamber 174. Extending downwardly from the disk 162 in fluid communication with the chamber 174 is an actuator spout 176, and the assembly 100 has an air conduit or tubing 180 interposed between the second inspiratory cavity 113b and the valve 160 for conveying air between the cavity 113b and the chamber 170, as further discussed below.

As best seen in FIGS. 20 and 21, the valve 160 is inserted into the recess 140, so that the disk plug 172 is spaced about 0.5 mm to 3 mm from the expired air outlet 106, and the retention flange 166 is in frictional engagement with the frame 104 in the recess 140. As seen in FIG. 21, the pressure control valve 134 is coupled to the pressure control air outlet 133, and the flexible partition 105a is stretched and placed over the frame 104 to enclose and partially define the expiratory chamber 112. The inspiratory chamber frame 104a is secured over the expiratory chamber frame 104 with a number of elastic bands 180 (see FIGS. 11 to 14), such that the first inspiratory cavity 113a is defined by the partition 105a on the lower end, and by the internal inspiratory chamber wall 104e on the upper end. The second inspiratory cavity 113b is enclosed on the upper end by the flexible wall 105b, and fluid communication between the cavity 113b and the valve actuator chamber 174 is established by connecting an air tubing 180 from the cavity 113b to the chamber 174 by the actuator spout 176. The corrugated hoses 3, 36 are fluidically coupled respectively to the expiratory and inspiratory chamber 112, 113 at the expired air and inhalation air outlets 132, 135.

For operation, the user selects the threshold pressure in the expiratory chamber 112 by first adjusting the distance between the first and second magnets 154, 156 by rotating the magnet holding bolt 152 relative to the threaded central aperture 150. To increase the threshold pressure, the bolt 152 is rotated to position the second magnet 156 closer to the first magnet 154, and to reduce the threshold pressure, the bolt 152 is rotated in the opposite direction to place the second magnet 156 further away from the first magnet 154.

As best seen in FIG. 11, the user breathes the expired air into the connector 1, which is directed by the non-breathing valve assembly 2 to the corrugated hose 3 and into the expiratory chamber 112. With the disk plug 172 located close to the expired air outlet 106, and the expired air being released through the outlet 106 more slowly than entering the expiratory chamber 112, the chamber 112 becomes pressurized with the expired air during the initial phase of the expiration. The flexible partition 105a then expands into and pressurizes the inspiratory chamber cavities 113a, 113b in turn, and the flexible wall 105b also expands outwardly into the external environment. Pressurization of the inspiratory chamber transmits some of the inhalation air in the chamber to the valve actuator chamber 174 through the air tubing 180, expanding the valve membrane 170 to actuate the disk plug 172 to close the expired air outlet 106. Further expiration further pressurizes both the chambers 112, 113a, 113b, thereby providing positive airway pressure during the expiration. If the air pressure in the chamber 112 exceeds the preselected threshold pressure, the first magnet 154 and the valve plug 158 moves away from the second magnet 156 and the valve seat 144 to release air from the expiratory chamber 112, so as to reduce discomfort to the user.

During inspiration, the user inspires the inhalation air from the inspiratory chamber pressurized during the expiration, and thus receives a positive airway pressure during the inspiration. With continued inspiration and resulting depressurization of the inspiratory chamber, the valve actuator chamber 174 also becomes depressurized to remove the disk plug 172 from the expired air outlet 106, allowing the expired air to be released slowly from the expiratory chamber 112. With the resulting retraction of the flexible wall 105a with depressurization of the chamber 112, the negative pressure exerted on the inspiratory chamber 113 draws in air from the external environment through the one-way air inlet valve 108 into the first inspiratory cavity 113a.

As seen in FIG. 20, a diameter of the disk plug 172 is about two times greater than that of the expired air outlet 106. It has been appreciated that the greater the diameter of the plug 172 is relative to the outlet 106, the less force or pressure is required to actuate the plug 172 in closing the outlet 106. By selecting a larger diameter of the plug 172 relative to the outlet 106, the plug 172 does not immediately release the expired air from the expiratory chamber 112 at the beginning of the inspiration, with the result that pressurization in the chambers is maintained for some time after the inspiration begins.

Figure 22:
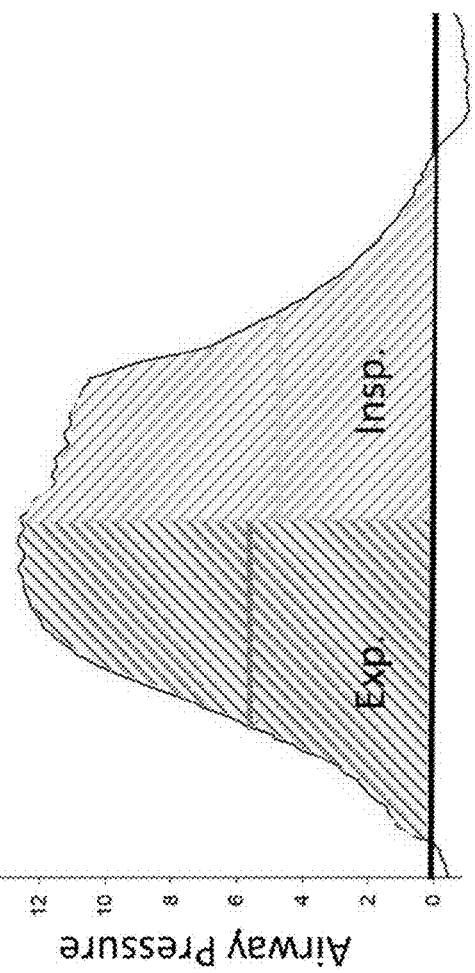
FIG. 22 shows a line graph illustrating an airway pressure (y-axis) during a single breath cycle, including an expiration phase and an inspiration phase.
Figure 23:
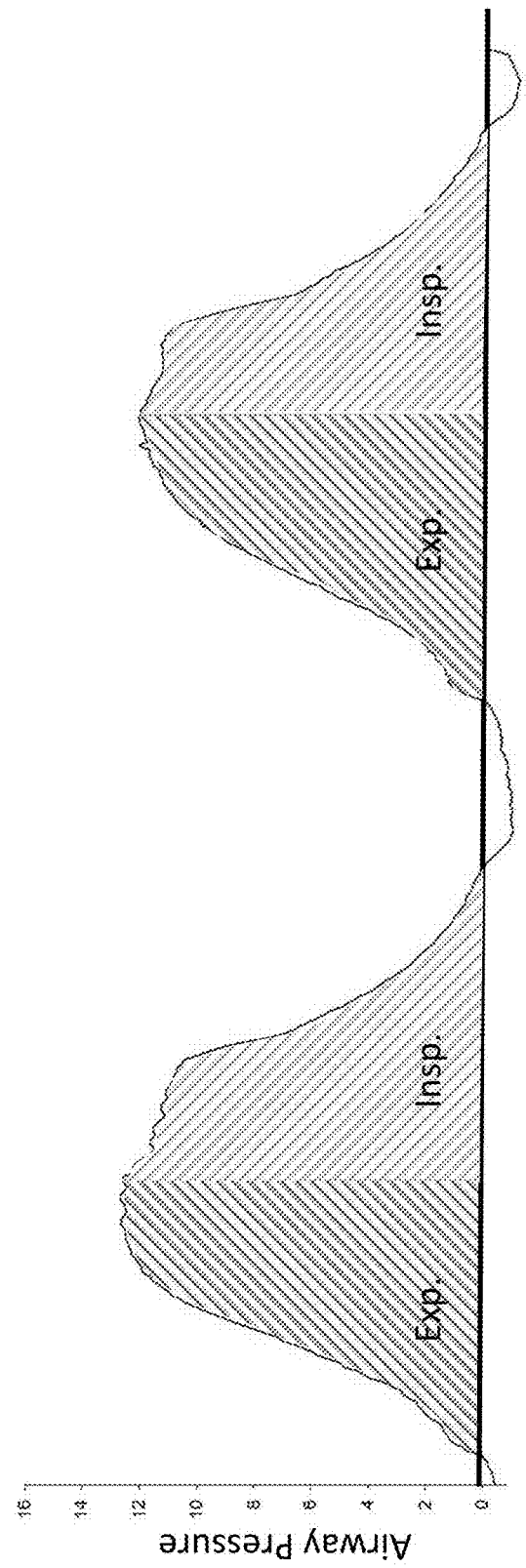
FIG. 23 shows a line graph illustrating an airway pressure (y-axis) during two breath cycles, with each breath cycle including an expiration phase and an inspiration phase.
Figure 24:
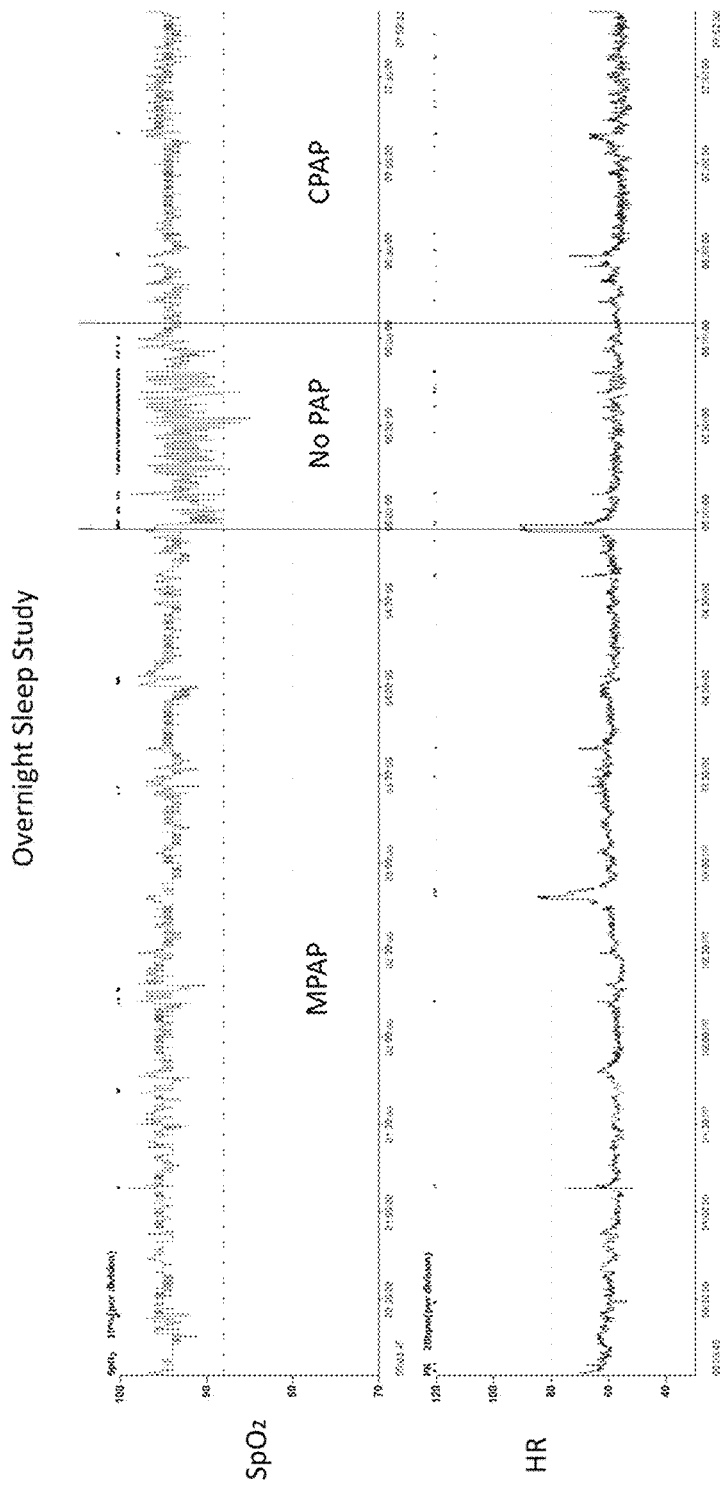
FIG. 24 shows a digital report generated by a pulse oximeter during an overnight sleep study performed with the positive airway pressure device shown in FIG. 11, and which includes a first line graph (top) showing a blood oxygen saturation level (y-axis) over time (x-axis), and a second line graph (bottom) showing a heart rate (y-axis) over time (x-axis)

For instance, FIGS. 22 and 23 show that positive airway pressure was provided by the device 50 over one or more breath cycles, specifically with increasing pressure towards the end of the expiration, and decreasing pressure towards the end of the inspiration. FIG. 24 shows a digital report generated by a wristband pulse oximeter (model designation: CMS-50F) during an overnight sleep study performed with the device 50 (labeled "MPAP"), as well as a commercially available continuous positive airway pressure ("CPAP") device, and no positive airway pressure device ("No PAP"). As shown in the upper line graph included in FIG. 23 illustrating a blood oxygen saturation level over time, and the lower line graph illustrating a heart rate over time, sleeping with the device 50 provided results similar to that obtained with the CPAP device.

Figure 25:
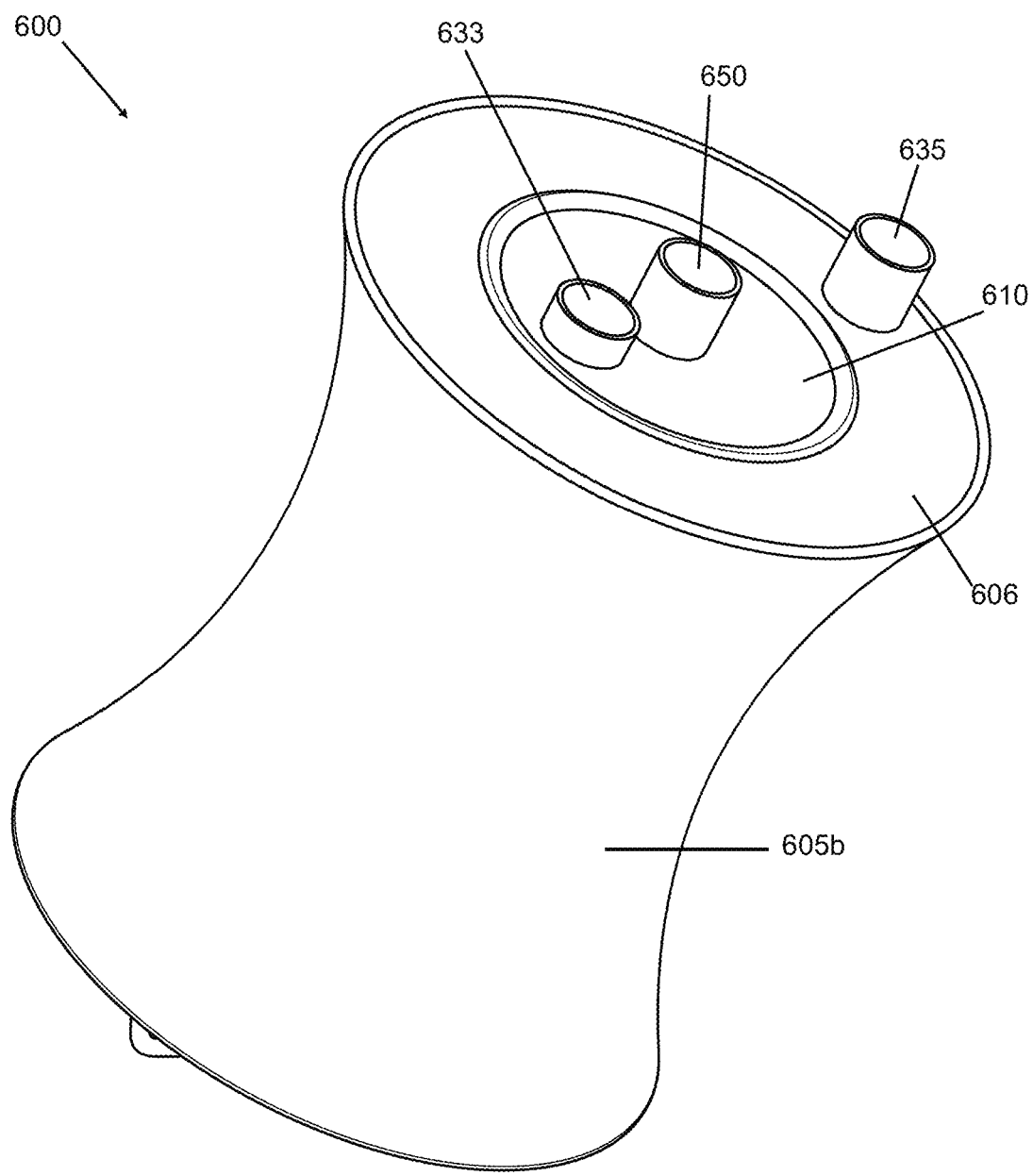
FIG. 25 shows a perspective view of a breath chamber assembly in accordance with a preferred embodiment of the invention.
Figure 26:
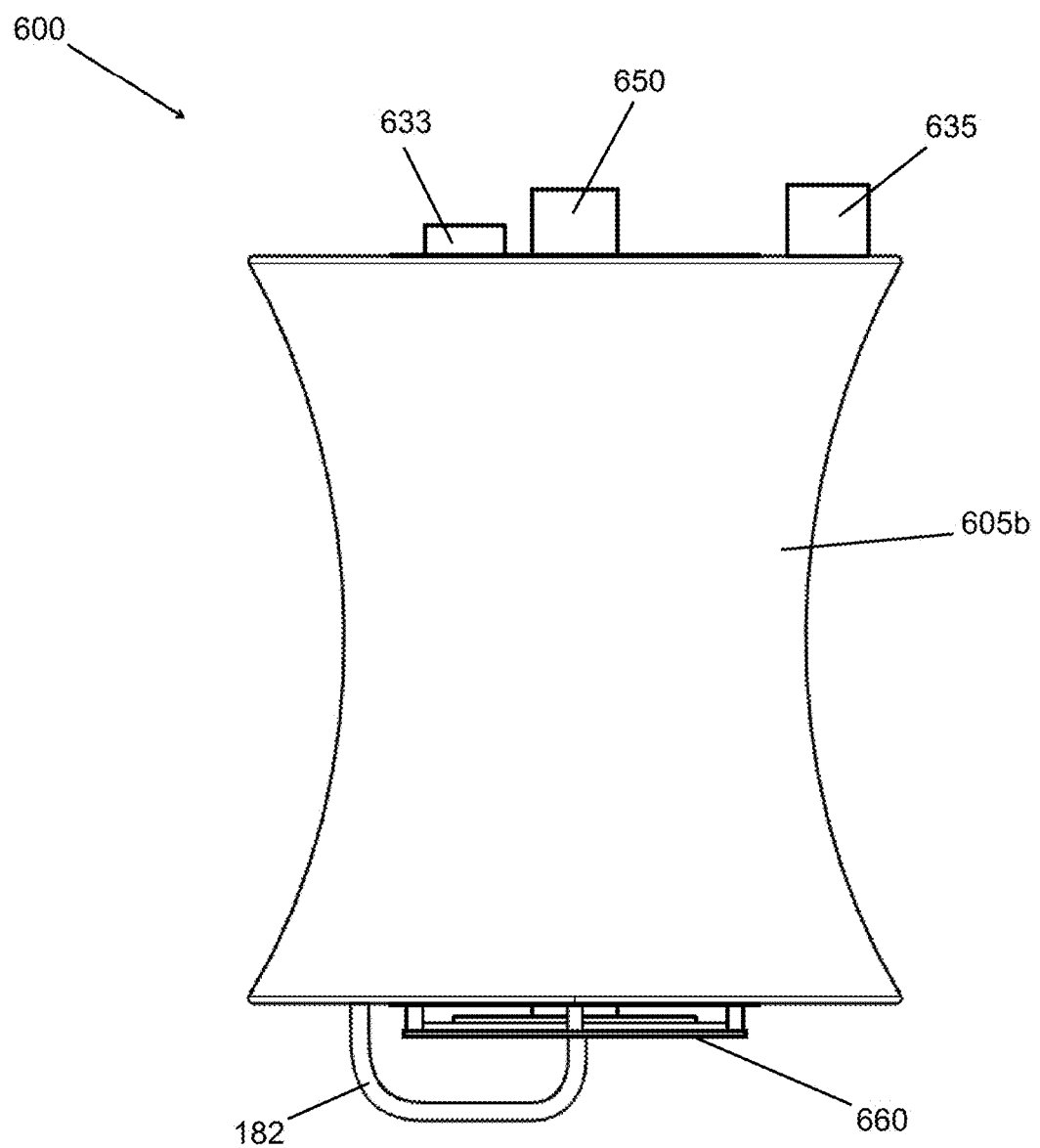
FIG. 26 shows an elevational view of the breath chamber assembly shown in FIG. 25.

A positive airway pressure device 500 in accordance with another preferred embodiment of the invention is illustrated in FIG. 25 which shows a perspective view of the device 500. The device 500 is similar in operation and construction to the device 50 in that the device 500 operates with actuation of a mushroom valve by a pressurized inspiratory chamber to pressurize an expiratory chamber during expiration, and is for use with the airway connector or airway connector assembly 1 as referenced above with respect to the device 50. The device 500 differs from the device 50, mainly in that in contrast to the device 50 where the expiratory and inspiratory chambers are disposed adjacent to each other, the inspiratory chamber in the device 500 is disposed around the periphery of the expiratory chamber.

Figure 27:
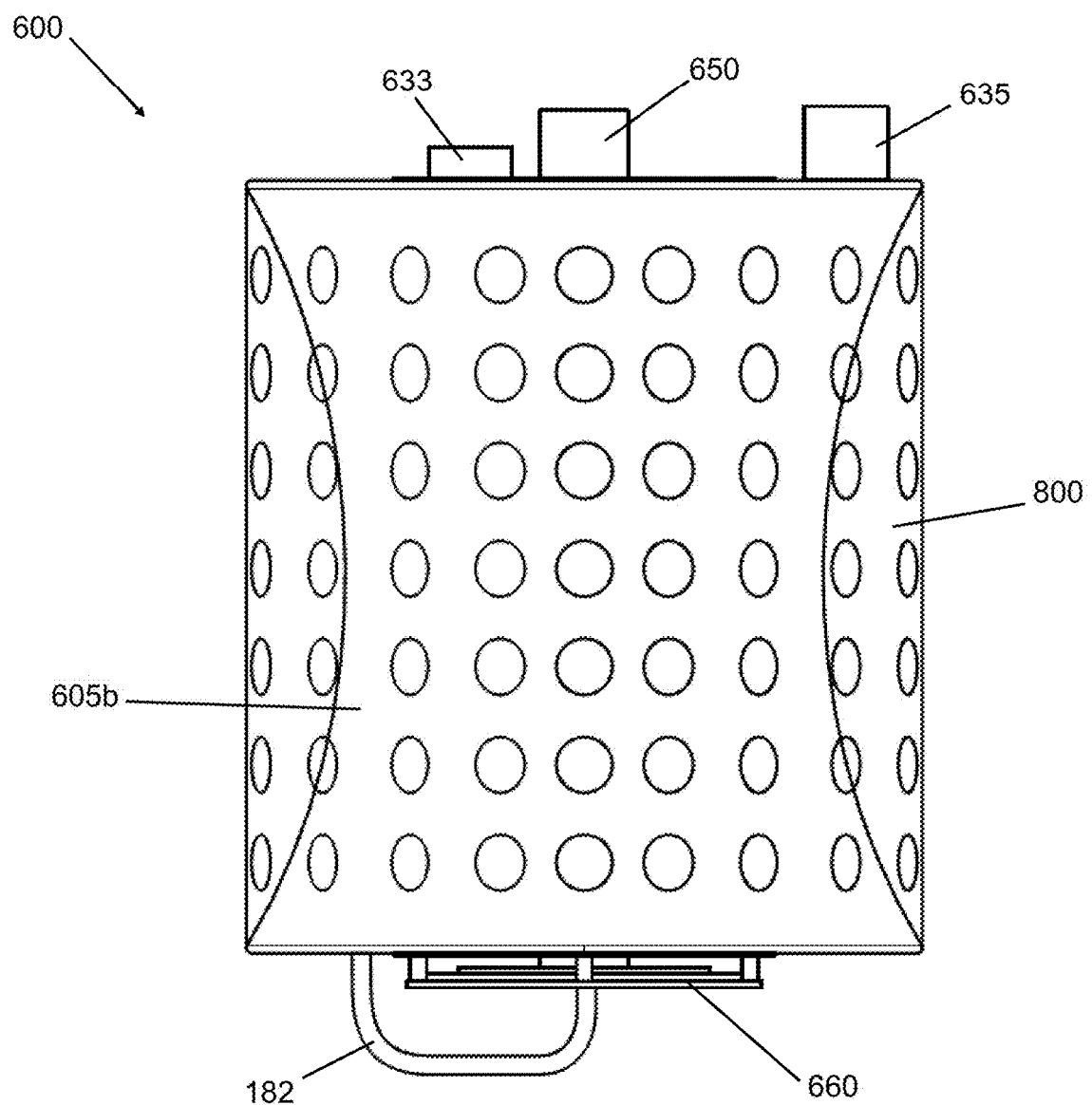
FIG. 27 shows another elevational view of the breath chamber assembly shown in FIG. 25 provided with an optional cover 800.
Figure 28:
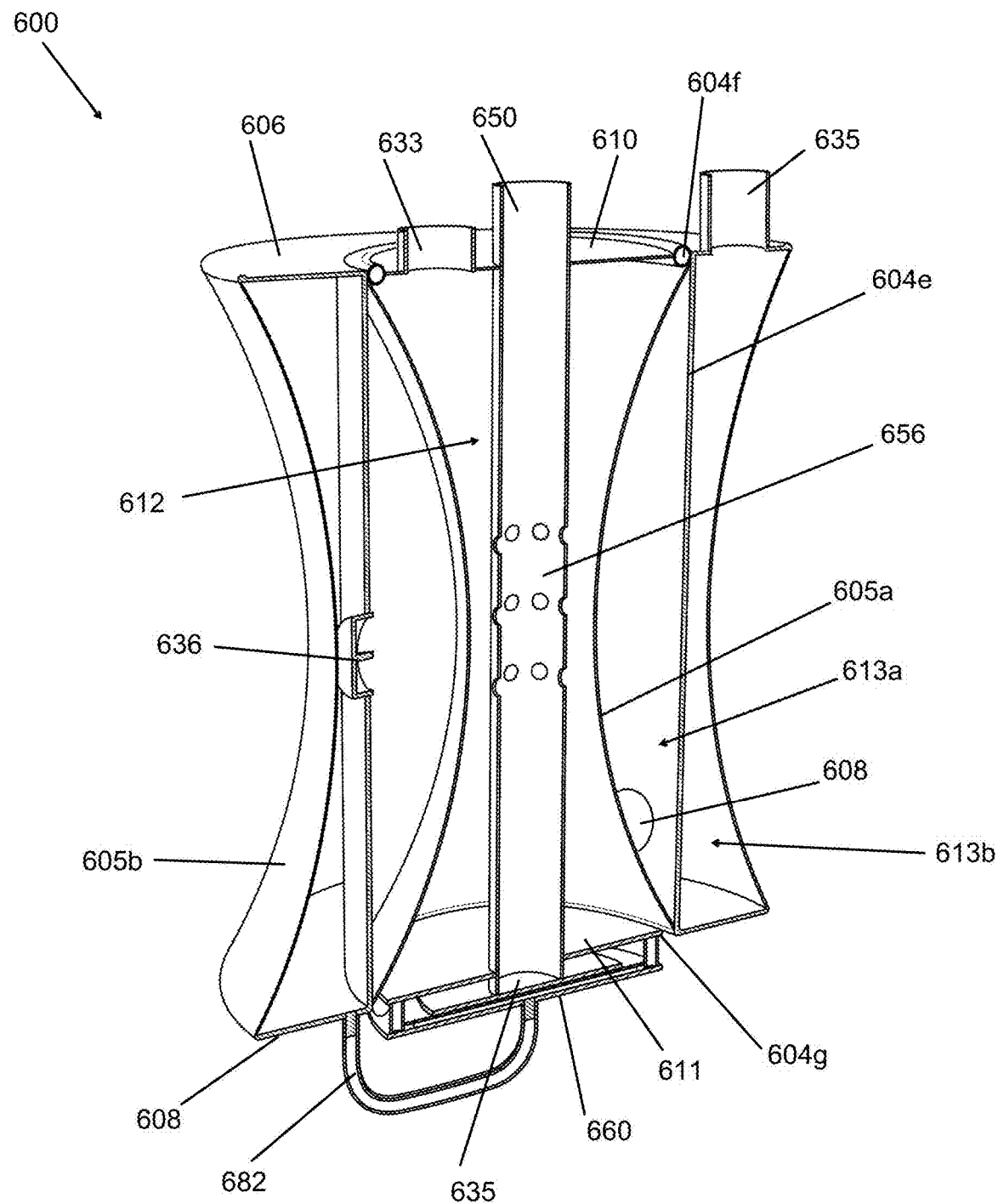
FIG. 28 shows a lateral cross-sectional perspective view of the breath chamber assembly shown in FIG. 25.

As best seen in FIG. 27, the device 500 has a breath chamber assembly 600 for fluid communication with the airway connector 1, and which is constructed with a generally cylindrical internal inspiratory chamber sidewall 604e having upper and lower longitudinal end rims 604f, 604g and a pair of inspiratory chamber flanges 606, 608 extending outwardly respectively from the outer peripheries of the rims 604f, 604g. The assembly 600 also has a pair of expiratory chamber end caps 610, 611 shaped to abut the inner peripheries of the rims 604f, 604g, respectively. The assembly 600 also has a resiliently flexible tubular membrane or partition 605a generally in the shape of an open-ended tube, and which is stretched along the interior lumen of the sidewall 604e with one longitudinal end frictionally engaged between the cap 610 and the rim 604f, and the other end between the cap 611 and the end 604g. The length of the resiliently flexible partition 605a is shorter than that of the sidewall 604e, such that the partition 605a is stretched along the length of the sidewall 604e. In that arrangement, the partition 605a defines an expiratory chamber 612 therein, which is enclosed on longitudinal ends by the end caps 610, 611.

The assembly 600 defines an inspiratory chamber having first and second inspiratory cavities 613a, 613b, with the cavity 613a defined by the partition 605a and the sidewall 604e, and the cavity 613b defined by the sidewall 604e, the flanges 606, 608, and a resiliently flexible sidewall or wall 605b of an open-ended tube shape. The longitudinal ends of the sidewall 605b are secured to the circumferential edges of the flanges 606, 608. Similar to the partition 605a, the length of the sidewall 605b is shorter than that of the inspiratory chamber sidewall 604e, such that the sidewall 605b is stretched along the length of the sidewall 604e.

The assembly 600 includes a substantially vertically oriented expired air duct 650 extending through the expiratory chamber 612, and is received through duct receiving apertures (not shown) defined by the end caps 610, 611. The duct 650 includes a perforated portion 656 along a length thereof to permit the expired air to be communicated from inside the duct 650 to the expiratory chamber 612 during expiration, as further described below.

Similar to the device 50, the end cap 610 defines a pressure control air outlet 633 for connecting to a pressure control valve (not shown), similar to the pressure control air outlet 133 and the pressure control valve 134, described above. The inspiratory chamber flange 608 has a low-resistance one-way air inlet valve 608, and the flange 606 defines an inhalation air outlet 635, respectively similar to the air inlet valve 108 and the inhalation air outlet 135, described above. The assembly 600 is also provided with a one-way inspiratory chamber valve 608 disposed in the inspiratory chamber sidewall 604e in fluid communication with the external environment, similar to the inspiratory chamber valve 136, noted above. The assembly 600 also has a poppet valve 660 and an air conduit or tubing 682, similar to the valve 160 and the air tubing 182 noted above.

On the other hand, an expired air inlet similar to the inlet 132 is not separately defined, and rather, is formed by an axial end portion of the expired air duct 650 extending outwardly from the end cap 610. Likewise, an expired air outlet similar to the outlet 106 is not separately defined, and rather, is defined by the other axial end portion of the duct 650 extending outwardly from the other end cap 611, located proximate to the poppet valve 660.

During operation, the expired air from the user is communicated and directed by the airway connector 1, the non-breathing valve assembly 2 and the corrugated hose 3 through the expired air duct 650, whereby the expired air is released into the expiratory chamber 612 at the perforated portion 656 and to the external environment at the open axial end of the duct 650 proximate the poppet valve 660. With slower release of the expired air to the external environment, the resiliently flexible partition 605a expands outwardly to pressurize the inspiratory cavities 613a, 613b, actuating the poppet valve 660, and thereby, pressurizing both the expiratory and inspiratory chambers 612, 613a, 613b with further expiration. During inspiration, the user receives the inhalation air from the pressurized inspiratory chamber, and depressurization of the inspiratory chamber by the inspiration opens the poppet valve 660 to release the expired air from the expiratory chamber 612. Negative pressure in the inspiratory chamber created by the depressurization of the expiratory chamber 612 and thus retraction of the partition 605a away from the inspiratory chamber 613 draws in air from the external environment through the air inlet valve 608 into the inspiratory cavity 613a.

It is to be appreciated while the assemblies 100, 600 are respectively described and shown as including the inspiratory chamber or chamber cavity having the low-resistance one-way air inlet valves 108, 608, the assemblies 100, 600 may not include the valves 108, 608. In an alternative embodiment, the airway connector 1 and/or the non-breathing valve assembly 2 may be provided with the air inlet valve to allow air from the external environment closer to the user to be inspired by the user under the positive pressure of the inspiratory chamber.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

The invention claimed is:

1. A breath powered positive airway pressure device comprising an airway connector assembly for communicating air to and from a user, and a breath chamber assembly in fluid communication with the airway connector assembly, the breath chamber assembly being for increasing airway pressure during expiration and inspiration, wherein the breath chamber assembly comprises an expiratory chamber for receiving expired air from the user, an inspiratory chamber for holding inhalation air to be inspired by the user, and a resiliently flexible partition separating the expiratory and inspiratory chambers, and the airway connector assembly comprises an airway connector for directing the expired air from and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector, wherein the breath chamber assembly further comprises: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough; and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet, wherein during said expiration, the flexible partition expands into and pressurizes the inspiratory chamber, thereby actuating the pneumatic valve to the closed position, and pressurizing the expiratory chamber, and wherein during said inspiration, the inspiratory chamber is depressurized, whereby the pneumatic valve moves to the open position to permit the expired air to be released through the air outlet, and depressurize the expiratory chamber.

2. The positive airway pressure device of claim 1, wherein at least one of the air outlet and the pneumatic valve are configured to release the expired air from the expiratory chamber more slowly than the expired air enters the expiratory chamber at the beginning of said expiration, and wherein the pneumatic valve is configured to be in the closed position at least at the end of the expiration and the beginning of the inspiration.

3. The positive airway pressure device of claim 1, wherein the inspiratory chamber comprises a resiliently flexible wall configured to expand outwardly during said expiration.

4. The positive airway pressure device of claim 3, wherein the inspiratory chamber comprises first and second inspiratory cavities respectively in fluid communication with the one-way air inlet valve and the airway connector assembly, the flexible wall enclosing the second inspiratory cavity, and the inspiratory chamber further comprising a one-way inspiratory chamber valve permitting the inhalation air to pass from the first inspiratory cavity to the second inspiratory cavity, wherein during said expiration, the flexible partition expands into the first inspiratory cavity, thereby moving the inhalation air in the first inspiratory cavity towards the second inspiratory cavity, and expanding the flexible wall outwardly.

5. The positive airway pressure device of claim 4, wherein the inspiratory chamber further comprises an internal chamber wall dividing the first and second inspiratory cavities, the one-way inspiratory chamber valve being disposed in the internal chamber wall, and the internal chamber wall being shaped to prevent inward contraction of the flexible wall into the inspiratory chamber, and contact between the flexible wall and the flexible partition.

6. The positive airway pressure device of claim 1, wherein the breath chamber assembly further comprises an air conduit interposed between the inspiratory chamber and the pneumatic valve in fluid communication therewith, and the pneumatic valve comprises a poppet valve comprising a disk plug and a pneumatic valve actuator coupled to the plug, the actuator being in fluid communication with the air conduit, wherein the actuator is configured to actuate the plug to the closed position during said expiration, and to move the plug to the open position during said inspiration.

7. The positive airway pressure device of claim 6, wherein the disk plug comprises a contact surface positioned for the fluid sealing contact with the air outlet in the closed position, the contact surface having a surface area that is at least 1.2 times greater than the air outlet, and the valve actuator comprises an expandable membrane coupled to the plug, wherein during said expiration, the expandable membrane expands to move the plug in said fluid sealing contact with the air outlet in the closed position.

8. The positive airway pressure device of claim 1, wherein the breath chamber assembly further comprises a pressure control valve in fluid communication with the expiratory chamber, the pressure control valve being configured to open and release the expired air from the expiratory chamber when a pressure in the expiratory chamber exceeds a threshold pressure, and to close when the pressure in the expiratory chamber is at or below the threshold pressure.

9. The positive airway pressure device of claim 8, wherein the pressure control valve comprises a generally tubular housing having an inwardly extending valve seat along a length thereof, first and second magnets oriented in the housing to have an attractive force therebetween, and a stop plug coupled to the first magnet, the stop plug and the first magnet being biased towards a seated fluid sealing engagement with the valve seat, and the second magnet being distanced from the first magnet and the stop plug with the valve seat interposed therebetween, wherein the second magnet is positioned to permit the first magnet and the stop plug to be in the seated fluid sealing engagement with the valve seat when the expiratory chamber is at or below the threshold pressure, and to move away from the valve seat to release the expired air when the threshold pressure is exceeded in the expiratory chamber.

10. The positive airway pressure device of claim 9, wherein a distance between the first and second magnets avis adjustable to select the threshold pressure, the air outlet is adjustable to select a rate at which the expired air is released from the expiratory chamber, and at least one of the flexible partition and wall are adjustable to select a rate of pressurization in the expiratory chamber during said expiration.

11. The positive airway pressure device of claim 1, wherein the device is exclusively breath powered, and the expiratory and inspiratory chambers are configured to increase the airway pressure at least at the end of said expiration and the beginning of said inspiration, and the expiratory and inspiratory chambers are depressurized to a baseline pressure at the end of said inspiration.

12. A breath chamber assembly for increasing airway pressure during expiration and inspiration, the breath chamber assembly comprising an expiratory chamber for receiving expired air from the user, an inspiratory chamber for holding inhalation air to be inspired by the user, and a resiliently flexible partition separating the expiratory and inspiratory chambers, the breath chamber assembly further comprising: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough; and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet,
wherein during said expiration, the flexible partition expands into and pressurizes the inspiratory chamber, thereby actuating the pneumatic valve to the closed position, and pressurizing the expiratory chamber, and wherein during said inspiration, the inspiratory chamber is depressurized, whereby the pneumatic valve moves to the open position to permit the expired air to be released through the air outlet, and depressurize the expiratory chamber.

13. The breath chamber assembly of claim 12, wherein the breath chamber assembly is for use with an airway connector assembly comprising an airway connector for directing the expired air and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector.

14. The breath chamber assembly of claim 13, wherein the inspiratory chamber comprises a resiliently flexible wall configured to expand outwardly during said expiration.

15. The breath chamber assembly of claim 14, wherein the inspiratory chamber comprises first and second inspiratory cavities, the first inspiratory cavity being in fluid communication with the one-way air inlet valve, and the second inspiratory cavity being for fluid communication with the airway connector assembly, wherein the flexible wall encloses the second inspiratory cavity, and the inspiratory chamber further comprises a one-way inspiratory chamber valve permitting the inhalation air to pass from the first inspiratory cavity to the second inspiratory cavity, wherein during said expiration, the flexible partition expands into the first inspiratory cavity, thereby moving the inhalation air in the first inspiratory cavity towards the second inspiratory cavity, and expanding the flexible wall outwardly.

16. The breath chamber assembly of claim 15, wherein the inspiratory chamber further comprises an internal chamber wall dividing the first and second inspiratory cavities, the one-way inspiratory chamber valve being disposed in the internal chamber wall, and the internal chamber wall being shaped to prevent inward contraction of the flexible wall into the inspiratory chamber, and contact between the flexible wall and the flexible partition.

17. The breath chamber assembly of claim 12, wherein at least one of the air outlet and the pneumatic valve are configured to release the expired air from the expiratory chamber more slowly than the expired air enters the expiratory chamber at the beginning of said expiration, and wherein the pneumatic valve is configured to be in the closed position at least at the end of the expiration and the beginning of the inspiration.

18. The breath chamber assembly of claim 12, wherein the breath chamber assembly further comprises an air conduit interposed between the inspiratory chamber and the pneumatic valve in fluid communication therewith, and the pneumatic valve comprises a poppet valve comprising a disk plug and a pneumatic valve actuator coupled to the plug, the actuator being in fluid communication with the air conduit, wherein the actuator is configured to actuate the plug to the closed position during said expiration, and to move the plug to the open position during said inspiration.

19. The breath chamber assembly of claim 18, wherein the disk plug comprises a contact surface positioned for the fluid sealing contact with the air outlet in the closed position, the contact surface having a surface area that is at least 1.2 times greater than the air outlet, and the valve actuator comprises an expandable membrane coupled to the plug, wherein during said expiration, the expandable membrane expands to move the plug in said fluid sealing contact with the air outlet in the closed position.

20. The breath chamber assembly of claim 12, wherein the breath chamber assembly further comprises a pressure control valve in fluid communication with the expiratory chamber, the pressure control valve being configured to open and release the expired air from the expiratory chamber when a pressure in the expiratory chamber exceeds a threshold pressure, and to close when the pressure in the expiratory chamber is at or below the threshold pressure.

21. The breath chamber assembly of claim 20, wherein the pressure control valve comprises a generally tubular housing having an inwardly extending valve seat along a length thereof, first and second magnets oriented in the housing to have an attractive force therebetween, and a stop plug coupled to the first magnet, the stop plug and the first magnet being biased towards a seated fluid sealing engagement with the valve seat, and the second magnet being distanced from the first magnet and the stop plug with the valve seat interposed therebetween, wherein the second magnet is positioned to permit the first magnet and the stop plug to be in the seated fluid sealing engagement with the valve seat when the expiratory chamber is at or below the threshold pressure, and to move away from the valve seat to release the expired air when the threshold pressure is exceeded in the expiratory chamber.

22. The breath chamber assembly of claim 21, wherein a distance between the first and second magnets are adjustable to select the threshold pressure, the air outlet is adjustable to select a rate at which the expired air is released from the expiratory chamber, and at least one of the flexible partition and wall are adjustable to select a rate of pressurization in the expiratory chamber during said expiration.

23. The breath chamber assembly of claim 12, wherein the device is exclusively breath powered, and the expiratory and inspiratory chambers are configured to increase the airway pressure at least at the end of said expiration and the beginning of said inspiration, and the expiratory and inspiratory chambers are depressurized to a baseline pressure at the end of said inspiration.

24. A method of providing breath powered positive airway pressure, the method comprising: a) providing a breath powered positive airway pressure device comprising an airway connector assembly for communicating air to and from a user, and a breath chamber assembly in fluid communication with the airway connector assembly, the breath chamber assembly being for increasing airway pressure during expiration and inspiration, wherein the breath chamber assembly comprises an expiratory chamber for receiving expired air from the user, an inspiratory chamber for holding inhalation air to be inspired by the user, and a resiliently flexible partition separating the inspiratory and expiratory chambers, the inspiratory chamber having a resiliently flexible wall configured to expand outwardly during said expiration, and the airway connector assembly comprises an airway connector for directing the expired air from and the inhalation air to the user, a one-way expiration valve interposed between the airway connector and the expiratory chamber to permit the expired air to pass from the airway connector to the expiratory chamber, and a one-way inspiration valve interposed between the airway connector and the inspiratory chamber to permit the inhalation air to pass from the inspiratory chamber to the airway connector, wherein the breath chamber assembly further comprises: i) a one-way air inlet valve in fluid communication with the inspiratory chamber for permitting the inhalation air to enter the inspiratory chamber therethrough; ii) an air outlet in fluid communication with the expiratory chamber for releasing the expired air from the expiratory chamber therethrough; and iii) a pneumatic valve for closing the air outlet, the pneumatic valve being movable between an open position and a closed position, wherein the pneumatic valve is actuated by an air pressure in the inspiratory chamber towards the closed position in fluid sealing contact with the air outlet;

b) expiring into the airway connector, whereby the flexible partition expands into and pressurizes the inspiratory chamber, and the flexible wall expands outwardly, thereby actuating the pneumatic valve to the closed position, and pressurizing the expiratory chamber; and c) inspiring the inhalation air held in the pressurized inspiratory chamber through the airway connector, whereby the inspiratory chamber is depressurized, thereby moving the pneumatic valve to the open position to permit the expired air in the expiratory chamber to be released through the air outlet.

\* \* \* \* \*